(12) United States Patent
Kroll et al.

(10) Patent No.: US 8,401,637 B2
(45) Date of Patent: Mar. 19, 2013

(54) MEDIUM VOLTAGE THERAPY APPLICATIONS IN TREATING CARDIAC ARREST

(75) Inventors: Kai Kroll, Plymouth, MN (US); Mark Kroll, Crystal Bay, MN (US); Tom Bugliosi, Rochester, MN (US)

(73) Assignee: Galvani, Ltd., Maple Grove, MN (US)

( * ) Notice: Subject to any disclaimer, the term of this patent is extended or adjusted under 35 U.S.C. 154(b) by 1832 days.

(21) Appl. No.: 11/285,756

(22) Filed: Nov. 22, 2005

(65) Prior Publication Data

US 2006/0142809 A1 Jun. 29, 2006

Related U.S. Application Data

(60) Provisional application No. 60/630,993, filed on Nov. 24, 2004.

(51) Int. Cl.
*A61N 1/39* (2006.01)

(52) U.S. Cl. .......................................................... 607/5

(58) Field of Classification Search ................. 607/8, 28
See application file for complete search history.

(56) References Cited

U.S. PATENT DOCUMENTS

| | | |
|---|---|---|
| 3,638,656 A | 2/1972 | Grandjean et al. |
| 3,703,900 A | 11/1972 | Holznagel |
| 3,923,060 A | 12/1975 | Ellinwood, Jr. |
| 3,952,750 A | 4/1976 | Mirowski et al. |
| 4,003,379 A | 1/1977 | Ellinwood, Jr. |
| 4,146,029 A | 3/1979 | Ellinwood, Jr. |
| 4,181,133 A | 1/1980 | Kolenik et al. |
| 4,222,386 A | 9/1980 | Smolnikov et al. |
| 4,280,502 A | 7/1981 | Baker, Jr. et al. |
| 4,349,030 A | 9/1982 | Belgard et al. |
| 4,390,021 A | 6/1983 | Spurrell et al. |
| 4,398,536 A | 8/1983 | Nappholz et al. |
| 4,408,606 A | 10/1983 | Spurrell et al. |
| 4,488,553 A | 12/1984 | Nappholz et al. |
| 4,488,554 A | 12/1984 | Nappholz et al. |
| 4,552,561 A | 11/1985 | Eckenhoff et al. |

(Continued)

FOREIGN PATENT DOCUMENTS

| | | |
|---|---|---|
| EP | 0540266 | 5/1993 |
| WO | WO 93/01861 | 2/1993 |

(Continued)

OTHER PUBLICATIONS

European Search Report for European Application No. EP 05 85 2106 dated Oct. 28, 2008.

(Continued)

*Primary Examiner* — Niketa Patel
*Assistant Examiner* — Hiba El-Kaissi
(74) *Attorney, Agent, or Firm* — Patterson Thuente Christensen Pedersen PA

(57) ABSTRACT

A method and system for treating an individual experiencing cardiac arrest using an automatic external defibrillator (AED) includes placing a first and a second electrode of the AED in electrical communication with an exterior surface of the individual. A need to apply a high voltage defibrillation signal to the individual is automatically determined. The method also includes automatically causing the AED to apply a medium voltage therapy (MVT) signal through the first and the second electrodes to the individual. The MVT signal is applied to induce a hemodynamic effect in the individual. Alternatively, or additionally, the MVT signal is applied to induce a respiratory effect in the individual. Optionally, the MVT signal is applied before determining the need to apply the defibrillation signal.

23 Claims, 11 Drawing Sheets

U.S. PATENT DOCUMENTS

| | | | |
|---|---|---|---|
| 4,559,946 A | 12/1985 | Mower | |
| 4,572,191 A | 2/1986 | Mirowski et al. | |
| 4,623,248 A | 11/1986 | Sperinde | |
| 4,686,988 A | 8/1987 | Sholder | |
| 4,693,253 A | 9/1987 | Adams | |
| 4,774,950 A | 10/1988 | Cohen | |
| 4,823,800 A | 4/1989 | Compos | |
| 4,830,006 A | 5/1989 | Haluska et al. | |
| 4,945,909 A | 8/1990 | Fearnot et al. | |
| 4,969,873 A | 11/1990 | Steinbach et al. | |
| 4,986,270 A | 1/1991 | Cohen | |
| 4,996,984 A | 3/1991 | Sweeney | |
| 4,998,975 A | 3/1991 | Cohen et al. | |
| 5,018,522 A | 5/1991 | Mehra | |
| 5,041,107 A | 8/1991 | Heil, Jr. | |
| 5,042,497 A | 8/1991 | Shapland | |
| 5,087,243 A | 2/1992 | Avitall | |
| 5,098,442 A | 3/1992 | Grandjean | |
| 5,184,616 A | 2/1993 | Weiss | |
| 5,193,535 A | 3/1993 | Bardy et al. | |
| 5,193,537 A | 3/1993 | Freeman | |
| 5,207,219 A | 5/1993 | Adams et al. | |
| 5,220,917 A | 6/1993 | Cammilli et al. | |
| 5,222,480 A | 6/1993 | Couche et al. | |
| 5,230,336 A | 7/1993 | Fain et al. | |
| 5,265,600 A | 11/1993 | Adams et al. | |
| 5,282,836 A | 2/1994 | Kreyenhagen et al. | |
| 5,282,837 A | 2/1994 | Adams et al. | |
| 5,305,745 A | 4/1994 | Zacouto | |
| 5,314,448 A | 5/1994 | Kroll et al. | |
| 5,330,505 A | 7/1994 | Cohen | |
| 5,330,506 A | 7/1994 | Alferness et al. | |
| 5,330,509 A | 7/1994 | Kroll et al. | |
| 5,336,245 A | 8/1994 | Adams et al. | |
| 5,350,402 A | 9/1994 | Infinger et al. | |
| 5,376,103 A | 12/1994 | Anderson et al. | |
| 5,391,185 A | 2/1995 | Kroll | |
| 5,411,524 A | 5/1995 | Rahul | |
| 5,431,687 A | 7/1995 | Kroll | |
| 5,431,688 A | 7/1995 | Freeman | |
| 5,464,434 A | 11/1995 | Alt | |
| 5,499,971 A | 3/1996 | Shapland et al. | |
| 5,527,344 A | 6/1996 | Arzbaecher et al. | |
| 5,601,611 A | 2/1997 | Fayram et al. | |
| 5,607,385 A | 3/1997 | Francischelli et al. | |
| 5,607,454 A | 3/1997 | Cameron et al. | |
| 5,632,716 A | 5/1997 | Bui et al. | |
| 5,658,237 A | 8/1997 | Francischelli | |
| 5,662,689 A | 9/1997 | Elsberry et al. | |
| 5,700,281 A | 12/1997 | Brewer et al. | |
| 5,716,378 A | 2/1998 | Minten | |
| 5,716,379 A | 2/1998 | Bourgeois et al. | |
| 5,735,876 A | 4/1998 | Kroll et al. | |
| 5,782,883 A | 7/1998 | Kroll et al. | |
| 5,824,029 A | 10/1998 | Weijand et al. | |
| 5,871,510 A | 2/1999 | Kroll et al. | |
| 5,913,879 A | 6/1999 | Ferek-Petric et al. | |
| 5,925,066 A | 7/1999 | Kroll et al. | |
| 5,978,703 A | 11/1999 | Kroll et al. | |
| 6,167,306 A | 12/2000 | Kroll et al. | |
| 6,171,252 B1 | 1/2001 | Roberts | |
| 6,185,457 B1 | 2/2001 | Kroll et al. | |
| 6,230,056 B1 | 5/2001 | Kroll et al. | |
| 6,263,241 B1* | 7/2001 | Rosborough et al. | 607/6 |
| 6,298,267 B1 | 10/2001 | Rosborough et al. | |
| 6,314,319 B1* | 11/2001 | Kroll et al. | 607/5 |
| 6,351,670 B1 | 2/2002 | Kroll | |
| 6,438,419 B1 | 8/2002 | Callaway et al. | |
| 6,556,865 B2 | 4/2003 | Walcott et al. | |
| 6,560,484 B1 | 5/2003 | Kroll et al. | |
| 6,567,697 B1 | 5/2003 | Kroll et al. | |
| 6,577,102 B1 | 6/2003 | Vaisnys et al. | |
| 6,760,621 B2 | 7/2004 | Walcott et al. | |
| 6,853,859 B1 | 2/2005 | Kroll et al. | |
| 6,982,073 B2 | 1/2006 | Sabacky et al. | |
| 7,011,637 B2 | 3/2006 | Sherman et al. | |
| 7,035,684 B2 | 4/2006 | Lee | |
| 7,488,293 B2 | 2/2009 | Marcovecchio et al. | |
| 7,706,864 B2 | 4/2010 | Kroll et al. | |
| 7,787,942 B2 | 8/2010 | Chinchoy et al. | |
| 7,809,438 B2 | 10/2010 | Echt et al. | |
| 7,957,799 B2 | 6/2011 | Sullivan et al. | |
| 8,064,995 B1 | 11/2011 | Dupelle et al. | |
| 8,121,681 B2 | 2/2012 | Hampton et al. | |
| 8,160,703 B2 | 4/2012 | Stickney et al. | |
| 8,165,662 B2 | 4/2012 | Cinbis et al. | |
| 8,165,673 B2 | 4/2012 | Sherman et al. | |
| 2002/0156503 A1* | 10/2002 | Powers et al. | 607/5 |
| 2002/0161407 A1* | 10/2002 | Walcott et al. | 607/5 |
| 2004/0039313 A1* | 2/2004 | Sherman et al. | 601/21 |
| 2004/0044373 A1 | 3/2004 | Kroll et al. | |
| 2005/0197676 A1 | 9/2005 | Kroll et al. | |
| 2006/0142809 A1 | 6/2006 | Kroll et al. | |
| 2009/0177127 A1 | 7/2009 | Sherman et al. | |

FOREIGN PATENT DOCUMENTS

| | | |
|---|---|---|
| WO | WO93/06866 | 4/1993 |
| WO | WO 93/19809 | 10/1993 |
| WO | WO 97/15351 | 5/1997 |
| WO | WO 99/03534 A1 | 1/1999 |

OTHER PUBLICATIONS

Byron L. Gilman et al., Electrically Induced Chest Constrictions During Ventricular Fibrillation Produce Blood Flow, ACC (American College of Cardiology), Mar. 26, 2007, Presentation #1019-195, 2 pages.

Byron L. Gilman et al., Electrically Induced Chest Constrictions Produce Blood Flow During Ventricular Fibrillation Via Thoracic-Only Pump Mechanism, HRS (Heart Rhythm Society), May 9, 2007, 2 pages.

Hao Wang MD et al., Transthoracic Application of Medium Voltage Therapy for Treatment of Cardiac Arrest, AHA (American Heart Association), Nov. 2007, 2 pages.

Hao Wang, MD et al., Electrically Induced Chest Constrictions Produce Ventilation as Well as Cardiac Output, NAEMSP (National Association of Emergency Medical Service Physicians), Jan. 2008, 3 pages.

Byron L. Gilman et al., Medium Voltage Therapy Produces Blood Flow for Prolonged Duration after Brief VF, HRS (Heart Rhythm Society), May 2008, 2 pages.

Byron L. Gilman et al., Intracardiac Stimulation Produces Blood Flow During Ventricular Fibrillation, Cardiostim, Jun. 2008, 1 page.

Love et al., Recommendations for Extraction of Chronically Implanted Transvenous Pacing and Defibrillator Leads: Indications, Facilities, Training. Apr. 2000. vol. 23. No. 4. Part 1. pp. 421-552.

Geddes, L.A., et al., "Electrically Produced Artificial Ventilation," Perspective and Progress vol. 22, No. 5, pp. 263-271 (1988).

Geddes, L.A., et al., "Ventricular Defibrillation With Single and Twin Pulses of Half-sinusoidal Current," Journal of Applied Physiology, vol. 34, No. 1, Jan. 1973.

Glenn, William W.L. et al., "Twenty Years of Experience in Phrenic Nerve Stimulation to Pace the Diaphragm," PACE, vol. 9, Nov.-Dec. 1986, Part I.

KenKnight, B.H., et al., "Regional Capture of Fibrillating Right Ventricular Myocardium Evidence of an Excitable Gap in VF Using High Resolution Cardiac Mapping," J.A.C.C., Feb. 1994, p. 283A.

Kirchhof, C., et al., "Regional Entrainment of Atrial Fibrillation Studied by High-Resolution Mapping in Open-Chest Dogs," Circulation, vol. 88, No. 2, Aug. 1993.

Kugelberg, J., "Ventricular Defibrillation—A New Aspect," Acta Chirurgica Scandinavica, Suppl. No. 372, 1967.

Kugelberg, J. E., "Ventricular Defibrillation With Double Square Pulse," Medical& Biological Engineering, vol. 6, 1968.

Laghi, Franco, et al., "Comparison of Magnetic and Electrical Phrenic Nerve Stimulation in Assessment of Diaphragmatic Contractility," Appl. Physiol. 80(5): 1731-1742 1996.

Leng, Charles T. M.D., et al., "Electrical Induction of Ventricular Fibrillation for Resuscitation From Postcountershock Pulseless and Asystolic Cardiac Arrests," Circulation pp. 723-728 (Aug. 7, 2001).

Murakawa, Yuji, et al. "The Effect of an Unsuccessful Subthreshold Shock on the Energy Requirement for the Subsequent Defibrillation." American Heart Journal, May 1989.

Quinn, et al., "Need for Sedation in a Patient Undergoing Active Compression—Decompression Cardiopulmonary Resuscitation," Academic Emergency Medicine, vol. 1, No. 5, pp. 463-467, Sep./Oct. 1994.
Resnekov, L., "Ventricular Defibrillation by Monophasic Trapezoidal-shaped Double-pulses of Low Electrical Energy," Cardiovascular Research, 2, 1968a.
Koster, Limited 'hands-off' periods during resuscitation. 2003. pp. 275-276.
Snyder, "Wide variation in cardiopulmonary resuscitation interruption intervals amoung commercially available automated external defibrillators may affect survival despite high defibrillation efficacy", 2004. vol. 32, No. 9. pp. S421-S424.
Aufderheide TP, et al., "Death by hyperventilation: A common and life threatening problem during cardiopulmonary resuscitation." Wolf Creek VII, Ranch Mirage, CA Jun. 13-16, 2003.
Hiba El-kaissii Berg, RA et al., "Precountershock cardiopulmonary resuscitation improves ventricular fibrillation median frequency and myocardial readiness for successful defibrillation from prolonged ventricular fibrillation: a randomized, controlled swine study." Ann E, 2004.
Cobb LA, et al., "Influence of cardiopulmonary resuscitation prior to defibrillation in patients with out-of-hospital ventricular fibrillation." JAMA Apr. 7, 1999; 281(13): 1182-8.
Eftestol T, et al., "Effects of interrupting precordial compressions on the calculated probability of defibrillation success during out-of-hospital cardiac arrest," Circulation May 14, 2002; 105(19): 2270-3.
Mr. Fell's Electrical Machine described, Gentleman's Magazine, Apr. 2, 1792.
Gilman, Byron et al., "Intracardiac Stimulation Produces Blood Flow During Ventricular Fibrillation," Cardiostim, Jun. 2008, 1 page.
Gilman, Byron et al., "Medium Voltage Therapy Produces Blood Flow for Prolonged Duration after Brief VF," HRS, May 2008, 2 pages.
Idris AH, et al., "Effect of ventilation on resuscitation in an animal model of cardiac arrest," Circulation Dec. 1994; 90(6): 3063-9.
KenKnight, Bruce H., et al. "Regional Capture of Fibrillating Ventricular Myocardium: Evidence of an Excitable Gap." Circulation Research, vol. 77, No. 4, Oct. 1995.
Gilman, Byron et al., "Electrically Induced Chest Constrictions Produce Blood Flow During Ventricular Fibrillation Via Thoracic-Only Pump Mechanism," HRS, May 9, 2007, 2 pages.
Gilman, Byron et al., "Electrically Induced Chest Constrictions During Ventricular Fibrillation Produce Blood Flow," ACC, Mar. 26, 2007, Presentation #1019-195, 2 pages.
Abstract, MacDonald RD, et al., "Impact of prompt defibrillation on cardiac arrest at a major international airport," Prehosp Emerg Care 2002; 6: 1-5.
Abstract, Menegazzi, JJ et al., "Immediate defibrillation versus interventions first in a swine model of prolonged ventricular fibrillation," Resuscitation Nov. 2003; 59(2): 261-70.
Menegazzi, JJ et al., "Ventricular fibrillation scaling exponent can guide timing of defibrillation and other therapies," Circulation Feb. 24, 2004; 109(7): 926-31.
Murdock et al., "Augmentation of Cardiac Output by External Cardiac Pacing: Pacemaker-Induced CPR," Pacing and Clinical Electrophysiology, Jan. 1986, vol. 9, No. 1, Part 1, pp. 1-154.
Niemann, JT et al., "Immediate countershock versus cardiopulmonary resuscitation before countershock in a 5-minute swine model of ventricular fibrillation arrest." Ann Emerg Med Dec. 2000; 36(6): 543-6.
Paradis, NA, et al., "Coronary perfusion pressure and the return of spontaneous circulation in human cardiopulmonary resuscitation," J Am Med Assoc 1990; 263: 1106-13.
Rosborough JP et al., "Electrical therapy for post defibrillatory pulseless electrical activity." PACE 2000 (NASPE abstracts) p. 591.
Abstract, Sherman, LD, et al., "Ventricular fibrillation exhibits dynamical properties and self-similarity," Resuscitation 2000; 47: 163-73.
Abstract, Steen, S et al., "The critical importance of minimal delay between chest compressions and subsequent defibrillation: a haemodynamic explanation." Resuscitation Sep. 2003; 58(3): 249-58.
Abstract, Stotz M, et al., "EMS defibrillation-first policy may not improve outcome in out-of-hospital cardiac arrest," Resuscitation 2003; 58: 277-82.
Valenzuela, TD, et al., "Outcomes of rapid defibrillation by security officers after cardiac arrests in casinos." N Engl J Med 2000; 343: 1206-9.
Van Alem AP, et al., "Interruption of cardiopulmonary resuscitation with the use of the automated external defibrillator in out-of-hospital cardiac arrest," Ann Emerg Med Oct. 2003; 42(4): 449-57.
Walcott GP et al., "Effects of burst stimulation during ventricular fibrillation on cardiac function after defibrillation." Am J Physiol Heart Circ Physiol Aug. 2003; 285(2): H766-74.
Wang, HF, et al., "Effects of biphasic vs. monophasic defibrillation on the scaling exponent in a swine model of prolonged ventricular fibrillation," Acad Emerg Med 2001; 8: 771-780.
Wang, Hao MD et al., "Electrically Induced Chest Constrictions Produce Ventilation as Well as Cardiac Output," NAEMSP, Jan. 2008, 3 pages.
Wang, Hao MD et al., "Transthoracic Application of Medium Voltage Therapy for Treatment of Cardiac Arrest," AHA, Nov. 2007, 2 pages.
Abstract, Wik, L et al., "Delaying defibrillation to give basic cardiopulmonary resuscitation to patients with out-of-hospital ventricular fibrillation: a randomized trial," JAMA Mar. 19, 2003; 289(11): 1389-95.
Abstract, Xie, J, et al., "Spontaneous gasping generates cardiac output during cardiac arrest," Crit Care Med Jan. 2004: 32(1): 238-40. ScienceDirect. pp. 1-6, 2003.
U.S. Appl. No. 08/754,712, filed Dec. 6, 1996.
U.S. Appl. No. 09/139,822, filed Aug. 25, 1998.
U.S. Appl. No. 09/251,553, filed Feb. 17, 1999.
U.S. Appl. No. 09/277,311, filed Mar. 26, 1999.
U.S. Appl. No. 09/694,111, filed May 20, 2003.
U.S. Appl. No. 09/693,455, filed Oct. 20, 2000.
U.S. Appl. No. 09/393,443, filed Sep. 8, 1999.
U.S. Appl. No. 09/392,233, filed Sep. 8, 1999.
U.S. Appl. No. 08/931,233, filed Sep. 15, 1997.
U.S. Appl. No. 08/548,013, filed Oct. 25, 1995.
U.S. Appl. No. 08/548,014, filed Oct. 25, 1995.
U.S. Appl. No. 08/548,234, filed Oct. 25, 1995.
U.S. Appl. No. 09/139,316, filed Oct. 25, 1995.
U.S. Appl. No. 61/056,375, filed May 27, 2008.
U.S. Appl. No. 60/630,993, filed Nov. 24, 2004.
U.S. Appl. No. 09/693,551, filed Oct. 20, 2000.
U.S. Appl. No. 10/429,509, filed May 5, 2003.
U.S. Appl. No. 11/053,177, filed Feb. 8, 2005.
Weng et al., A Novel Electrical Therapy for Postshock PEA in a Porcine Model and abstract. 2011.
Gilman et al., "Applying the Principles of Functional Stimulation to Electrical CPR".2008. 2 pgs.
Gilman et al., "Electrically Induced Chest Constrictions Produce Ventilation As Well As Cardiac aOutput", Jan. 2008. 2 pgs.
Ristagno et al., "Transthoracic Applcation of Medium Voltage Therapy Maintains Forward Blood Flow During Cardiac Arrest", 2008. 2pgs.
Gilman, et al., Medium Voltage Therapy for Preventing and Treating Asystole and PEA and ICDs. 31st Annual International Conference. Sep. 2009. 3 pgs.
Wang et al, "Coronary Blood Flow Produced by Muscle Contractions Induced by Intracardiac Electrical CPR during Ventricular Fibrillation", Mar. 2009. vol. 32. 5 pgs.
Wang et al, Transthoracic Application of Electrical Cardiopulmonary Resuscitation for Treatment of Cardiac Arrest. Crit Care Med. 2008, vol. 36, No. 11. 9pgs.
Aufderheide, Tom P. M.D., "Pacemakers and Electrical Therapy During Advanced Cardiac Life Support," Respiratory Care Apr. '95 vol. 40. No. 4.
Bleske, et al., "Comparison of adrenergic agonists for the treatment of ventricular fibrillation and pulseless electrical activity," Resuscitation 28, pp. 239-251, Aug. 1994.
DeBehnke, Daniel, "Resuscitation time limits in experimental pulseless electrical activity cardiac arrest using cardiopulmonary bypass," Resuscitation 27, pp. 221-229, Feb. 28, 1994.

Schuder, J. C., et al., "Transthoracic Ventricular Defibrillation in the Dog With Unidirectional Rectangular Double Pulses," Cardiovascular Research, 4, 1970.

Wik, L, et al., "Rediscovery of the importance of compressions to improve outcome," Resuscitation 2003; 58: 567-9.

EP Application No. 05852106.3, Search Report dated Oct. 28, 2008, 2 pages.

Snyder, "Wide variation in cardiopulmonary resuscitation interruption intervals amoung commercially available automated external defibrillators may affect survival despite high defibrillation efficacy," 2004, vol. 32, No. 9, pp. S421-S424.

US 5,584,866, 12/1996, Kroll et al. (withdrawn)

* cited by examiner

ADVANCED MONITOR/DEFIBRILLATOR INTERFACE WITH PATIENT

NOTE: BLUETOOTH TECHNOLOGY COULD BE USED TO MINIMIZE ALL WIRE CONNECTIONS TO PATIENT EXCEPT THOSE TO DEFIBRILLATION/MVT PATCHES AND BLOOD PRESSURE MEASUREMENT SENSOR.

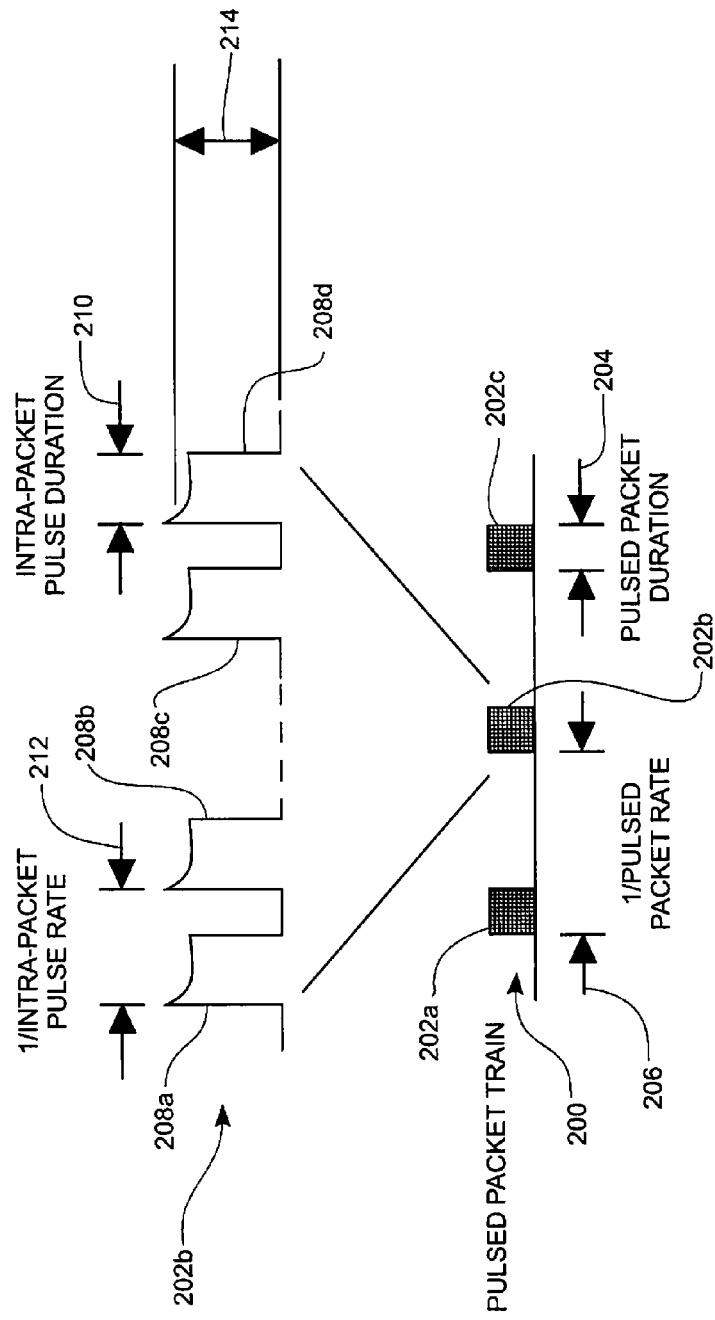

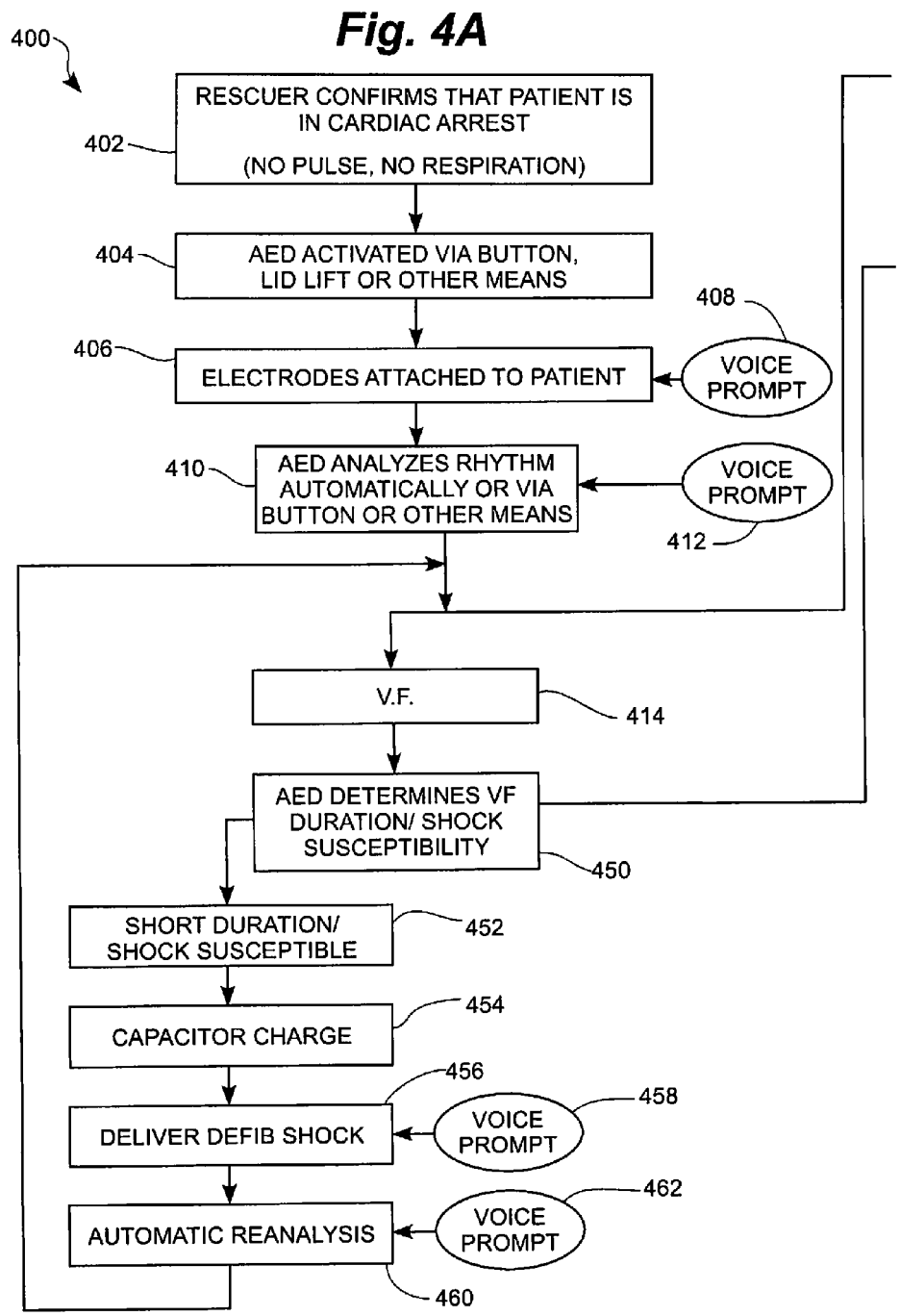

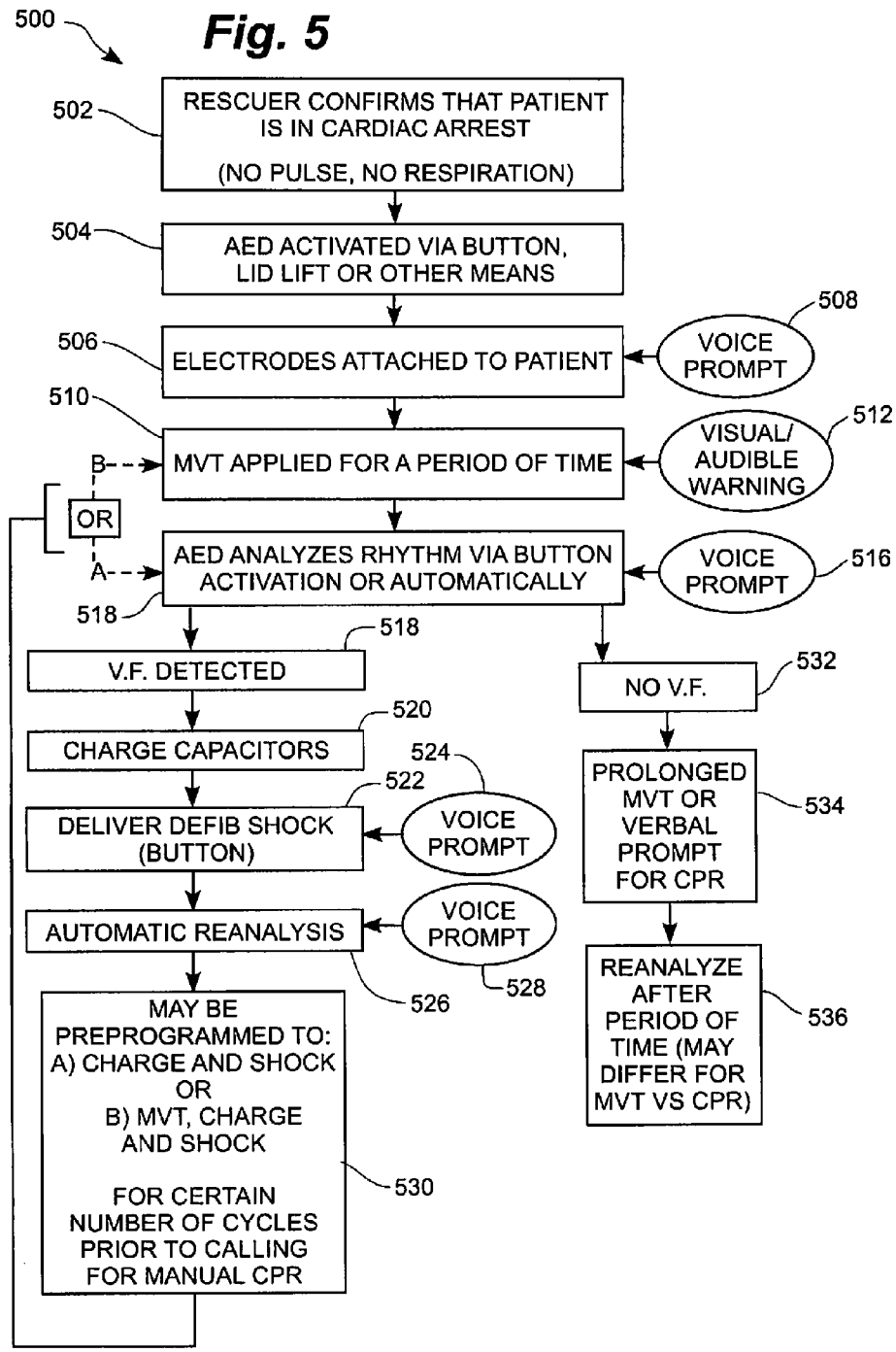

MEDIUM VOLTAGE THERAPY APPLICATIONS IN TREATING CARDIAC ARREST

RELATED APPLICATION

The present application claims the benefit of U.S. Provisional Application No. 60/630,993 filed Nov. 24, 2004, which is incorporated herein in its entirety by reference.

FIELD OF THE INVENTION

The invention relates generally to treatments for individuals experiencing cardiac arrest, and more particularly, to incorporating as part of an automatic external defibrillator (AED) the application of a medium voltage therapy (MVT) stimulation to an exterior of the patient in conjunction with, or in lieu of, externally-applied defibrillation therapy.

BACKGROUND OF THE INVENTION

Cardiac arrest is a significant public health problem cutting across age, race, and gender. A positive impact on cardiac arrest survival has been demonstrated with the substantial reduction in time to defibrillation provided by the widespread deployment of automated external defibrillators (AEDs). Examples of AEDs are described in U.S. Pat. Nos. 5,607,454, 5,700,281 and 6,577,102.

Optimal resuscitation therapy for out of hospital (OOH) cardiac arrest is the subject of substantial ongoing research. Research has been clear in demonstrating that the timing of resuscitation is of critical importance. For example, there is less than a 10% chance of recovery after just ten minutes after the onset of ventricular fibrillation (VF). This knowledge led to the recent widespread deployment of AEDs, primarily in public areas with a high population concentration such as airports and shopping malls. A positive impact on cardiac arrest survival has been demonstrated due to the substantial reduction in time to defibrillation as a result of more available access to AEDs.

Recent studies, however, have identified the importance of performing CPR-type chest compressions before defibrillation and minimizing the time to defibrillation shock following the cessation of the CPR chest compressions in facilitating effective recovery from VF episodes of especially long duration. It is generally believed that perfusion of the myocardium achieved during CPR preconditions the heart for the defibrillating shock. Despite the importance of CPR, implementation of CPR in the field is hampered by many problems including the dependence on rescuer technique, which is known to be variable even with trained professionals, fatigue over time, and attitude of the rescuer. Even in situations where an AED provides voice prompts instructing rescuers to administer CPR, rescuers perform CPR less than half the time in an actual rescue situation. A lack of understanding and fear of accidentally being subjected to energy from the defibrillation shock may make it difficult to induce non-professional rescuers using an AED to perform CPR up until the moment of defibrillation.

Conventional AEDs perform a cardiac rhythm analysis to determine if a patient has a condition that is treatable by a defibrillation shock. The cardiac rhythm analysis is performed just prior to shock delivery. Because CPR administered by a rescuer can interfere with a proper cardiac rhythm analysis, conventional AEDs provide a voice command prompt to stop performing CPR and not touch the patient during cardiac rhythm analysis. Some AEDs also utilize a time delay prior to delivering the defibrillating shock to reduce the risk of the non-professional rescuer being shocked. Studies have demonstrated that return of spontaneous circulation (ROSC) in the patient is most successful when defibrillation is administered during CPR. Furthermore, delays between CPR and defibrillation as short as 20 seconds have been shown to significantly reduce ROSC probabilities. Therefore, a need exists for a solution to minimize or eliminate such delays during rescue events utilizing AEDs.

The standard for electrical cardio-therapy administered from the exterior of the patient during ventricular fibrillation has been high-voltage, high-energy defibrillation signals. U.S. Pat. No. 6,298,267 describes the use of high-energy signals for treating ventricular fibrillation, and for restoring an effective cardiac output to relieve electromechanical dissociation or pulseless electrical activity conditions. For treating arrhythmia conditions, cardiac pacing therapy utilizing lower-voltage, lower-energy pacing signals is known. Externally applied pacing signaling functionality has been combined with defibrillation-type functionality in a single external device, as described in PCT Application, Publication No. WO 99/03534.

Cardiac electrotherapy signaling having an amplitude that is greater than that of pacing-type signaling, but less than the amplitude and energy level associated with defibrillation-type signaling, is known in the art as medium voltage therapy (MVT). For example, U.S. Pat. No. 5,314,448 describes delivering low-energy pre-treatment pulses followed by high-energy defibrillation pulses, utilizing a common set of electrodes for both types of signals. According to one therapeutic mechanism of this pre-treatment, the MVT pulses re-organize the electrical activity within the cardiac cells of the patient to facilitate a greater probability of successful defibrillation with a follow-on defibrillation pulse. U.S. Pat. No. 6,760,621 describes the use of MVT as pretreatment to defibrillation that is directed to reducing the likelihood of pulseless electrical activity and electromechanical dissociation conditions as a result of the defibrillation treatment. The mechanism by which these results are achieved by MVT has been described as a form of sympathetic stimulation of the heart. These approaches are directed to influencing the electrochemical dynamics or responsiveness of the heart tissues.

MVT has also been recognized as a way of forcing some amount of cardiac output by electrically stimulating the heart directly with signals that cause the heart and skeletal muscles to expand and contract in a controlled manner. See U.S. Pat. Nos. 5,735,876, 5,782,883 and 5,871,510. These patents describe implantable devices having combined defibrillation, and MVT capability for forcing cardiac output. U.S. Pat. No. 6,314,319 describes internal and external systems and associated methods of utilizing MVT to achieve a hemodynamic effect in the heart as part of an implantable cardioverter defibrillator (ICD) for purposes of achieving a smaller prophylactic device. The approach described in the '319 patent uses the MVT therapy to provide a smaller and less expensive implantable device that can maintain some cardiac output without necessarily providing defibrillation therapy.

One drawback associated with the existing MVT approaches for forcing cardiac output is they are not well-suited for out-of-hospital or external treatments. In the case of the MVT therapy described in the '319 patent, an implantable device must be implanted in each patient. The '319 patent expressly teaches that MVT therapy is not relevant to external devices, because such external devices are too slow in their arrival and use with a patient.

While developments in defibrillator technology, both automatic external defibrillators (AEDs) and implantable cardioverter defibrillators (ICDs) have made great strides in aiding the electrical cardiac resuscitation of individuals experiencing cardiac arrest, a need exists for a solution that can effectively induce respiration in a patient while electrically inducing coronary output in out-of-hospital rescue situations.

SUMMARY OF THE INVENTION

The present invention provides for methods and systems for treating an individual experiencing cardiac arrest using an automatic external defibrillator (AED) that selectively incorporates the use of medium voltage therapy (MVT) to preferably induce both a hemodynamic effect and a respiratory effect in that individual. A method utilizing this invention includes placing a first and a second electrode of an AED in electrical communication with an exterior surface of the patient and automatically selectively causing the AED to apply a medium voltage therapy (MVT) signal through the first and the second electrodes to the patient. The MVT signal is applied to preferably induce both a hemodynamic effect and a respiratory effect in the individual. The method also includes automatically selectively causing the AED to administer a high voltage defibrillation signal to the individual if cardiac resuscitation is indicated.

In a preferred embodiment of the invention, treatment includes detecting an absence of normal cardiac activity in the individual. If appropriate, the AED applies a MVT signal through an exterior surface of the individual. The AED also determines whether to apply a defibrillation signal to the patient. Preferably, the MVT signal application is initiated before the indication for applying a defibrillation signal is determined.

Another aspect of the invention is directed to a method and AED for treating an individual experiencing cardiac arrest. This aspect includes the AED detecting an absence of normal cardiac activity in the patient. The AED applies a MVT signal to the patient, and monitors a patient characteristic that is indicative of a therapeutic effectiveness of the MVT signal. Preferably, in this embodiment at least one wave-shaping parameter of the MVT signal is adjusted while the MVT is being administered. The ability to adjust a wave-shaping parameter without necessarily increasing an amplitude of the MVT signal permits refinement of the MVT therapy without encountering the increased pain experienced by an individual in response to signals having an increased amplitude.

Another aspect of the invention is the development of a "training only" version of the invention that simulates the visual and auditory functioning of the device while not providing any actual electrical output. This device allows rescuers to get comfortable with the actual working of an AED with the incorporated MVT therapy. Preferably, this embodiment includes appropriate and relevant feedback and training responses to confirm proper usage of the device and correct improper usage of the device.

BRIEF DESCRIPTION OF THE DRAWINGS

The invention may be more completely understood in consideration of the following detailed description of various embodiments of the invention in connection with the accompanying drawings, in which:

FIG. 2 is a timing diagram illustrating variable waveform parameters of MVT signaling according to one aspect of the invention.

FIG. 5 is a flow diagram illustrating a rescue sequence according to one aspect of the invention in which MVT is applied as early as possible to the patient in order to address the problem of therapy delay due to rhythm analysis.

Figure 1A:
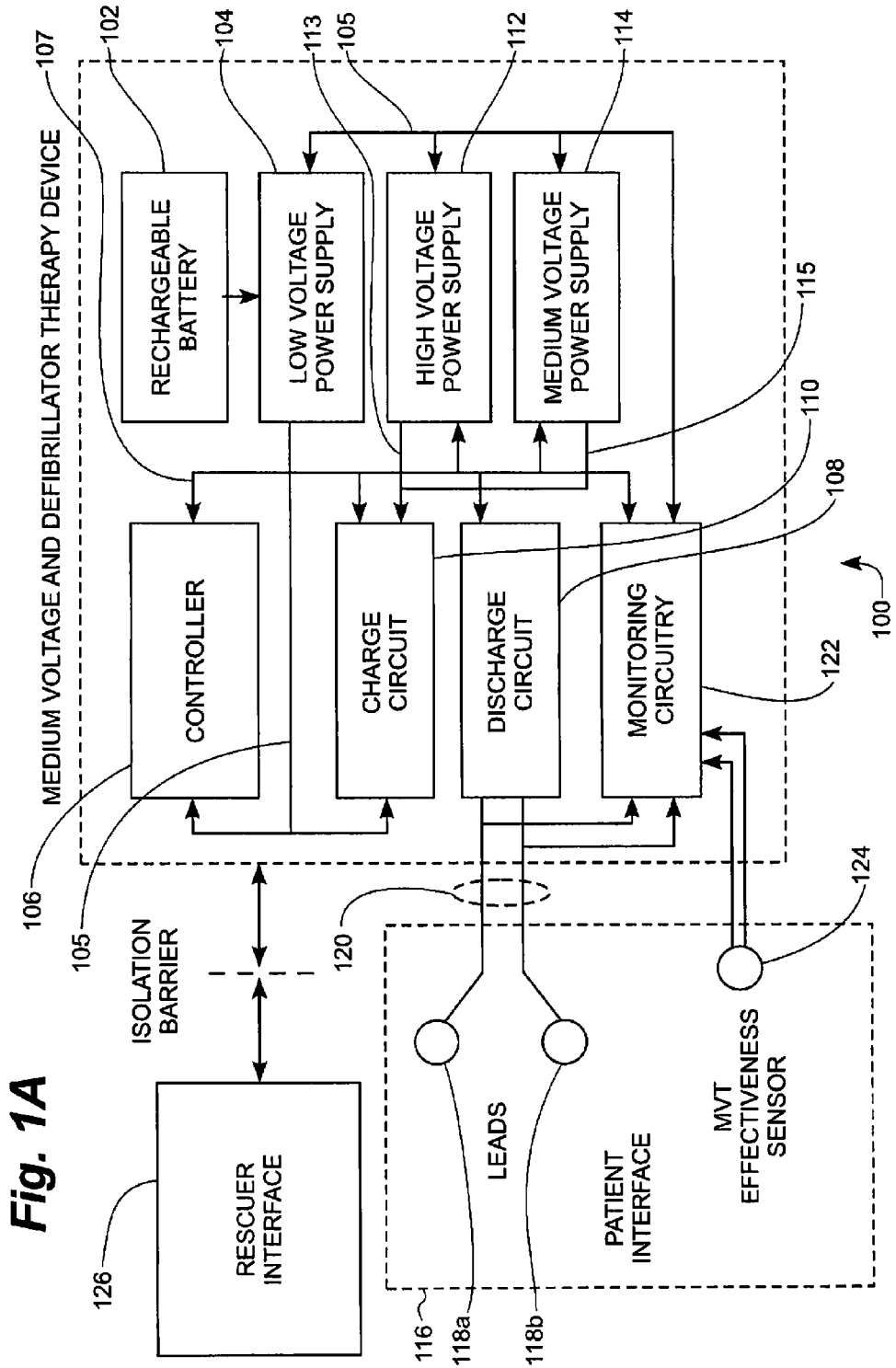
FIG. 1A is a block diagram illustrating an automatic external defibrillator (AED) incorporating medium voltage therapy (MVT) according to one embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

One aspect of the present invention is directed to an automated substitute for chest compressions. In one embodiment, an automatic external defibrillator (AED) is equipped with a capability of automatically providing Medium Voltage Therapy (MVT) via its defibrillation patch electrodes associated with the AED. The combination of an AED with MVT provides a substitute and/or enhancement to mechanical chest compression that has a potential to significantly improve post-resuscitation survival rates. In one example embodiment, the MVT provides electrical stimulation in an individual's chest region that elicits muscular contractions which, in turn, create a hemodynamic effect that results in an enhanced opportunity for coronary perfusion and create an opportunity for respiration of the lungs in response to those muscular contractions as well as the electrical stimulation.

There are various mechanisms by which MVT operates to achieve coronary perfusion and/or respiration in the individual. These include contributions from both direct cardiac and thoracic muscle stimulation, and an additional sympathetic stimulation that increases cardiac myocyte contractility and excitability. Specifically, cardiac and thoracic muscle stimulation is preferably accomplished by: (1) stimulation of resting cells (in "phase 4") so that they contract; (2) stimulation of cells late in their contraction phase ("phase 3) so that they extend their contraction time and thus help "splint" the heart to take advantage of those cells in phase 4 beginning a new contraction; (3) contracting chest muscles to give a partial chest contraction; and (4) stimulation of the phrenic nerve to give a diaphragmatic contraction which reduces pressure in the chest and "sucks" blood back into the heart to facilitate its pumping out.

In another aspect of the invention, MVT is utilized for electrically inducing respiration in a patient by way of electrical stimulation of an individual and/or patient. The term patient may be utilized in describing the present invention, although it will be understood that the individual for whom the treatment is applied may or may not be a person already under medical care at the time the treatment is performed. One mechanism by which MVT operates to achieve respiration in the individual/patient is by stimulation of the phrenic nerve. Another mechanism includes causing muscles in the chest, abdominal area, or diaphragm of the patient to expand and contract, causing ventilation in the patient.

FIG. 1A is a diagram illustrating an example AED 100 that utilizes MVT according to one embodiment. AED 100 is preferably a hand-portable instrument that is self-powered from an optionally-rechargeable battery 102. Battery 102 provides an energy source that can be converted and conditioned for powering the various circuitry of AED 100. A low voltage power supply 104 converts the battery power into one or more stabilized power supply outputs 105 for supplying the power to the subsystems of AED 100. The subsystems include a controller 106, such as, for example, microprocessor that is programmed and interfaced with other subsystems to control most of the functionality of AED 100.

Persons skilled in the art will recognize that the controller 106 can take on a variety of forms within the spirit of the invention. For example, in addition to a microprocessor that executes software instructions, the controller can be in the form of a hardware logic circuit, such as a programmable logic device (PLA/PAL), an application-specific integrated circuit (ASIC), a field-programmable logic array (FPGA), or any set of interconnected logic circuits, and the like. Also, the controller 106 can include a combination of hardware and software logic, such as a dynamically-reprogrammable ("on the fly") logic device. Furthermore, the controller 106 can be implemented with a combination of a plurality of individual controller components, such as with dual microprocessors or with a microprocessor/ASIC/FPGA combination.

In the embodiments in which the controller 106 is implemented as a microprocessor or microcontroller, the microprocessor interface includes data and address busses, optional analog and/or digital inputs, and optional control inputs/outputs, collectively indicated at microprocessor interface 107. In one example embodiment, the microprocessor is programmed to control the sequence of the electrotherapy, as well as the output waveform parameters. The user input to the system can be in the form of simple pushbutton commands, or voice commands.

Example AED 100 includes a discharge circuit 108 for administering therapeutic signals to the patient. Discharge circuit 108 controls the release of therapeutic energy to achieve a desired signal having a particular waveform and energy. Charge circuit 110 energizes discharge circuit 108 to achieve the desired output signal. High voltage power supply 112 provides a sufficient energy source 113 to charge circuit 110 to enable charge circuit 110 and discharge circuit 108 to ultimately deliver one or more defibrillation pulses to an exterior surface of the patient. Typically, a voltage sufficient to achieve a therapeutic defibrillation signal from an exterior of the patient is in the range of 1 kV-3 kV.

In accordance with this embodiment, AED 100 also includes a medium voltage power supply 114. Medium voltage power supply 114 provides a medium voltage source 115 that enables charge circuit 110 and discharge circuit 108 to ultimately deliver one or more MVT signals to the exterior of the patient. In one embodiment, the medium voltage power supply is adapted to provide a regulated voltage in the range from 20-1000 V.

The defibrillation and MVT signals are administered to the patient via patient interface 116. In one embodiment, patient interface 116 includes electrodes 118a and 118b that are adhesively applied to the patient's chest area. Electrodes 118a and 118b are electrically coupled, such as by insulated copper wire leads 120, to discharge circuit 108. In one example embodiment, electrodes 118a and 118b can deliver the defibrillation signals and the MVT signals. In an alternative example embodiment, separate sets of electrodes (not shown) are used for the defibrillation and MVT signals, respectively. One advantage of separate electrode sets is an ability to produce different therapeutic current paths through the patient without having to re-position the electrodes for administering each corresponding type of therapeutic signal.

Electrodes 118a and 118b are also utilized for obtaining information about the patient's condition. For example, electrodes 118 can be used to monitor the patient's cardiac rhythm. Signals originating in the patient that are measured by electrodes 118 are fed to monitoring circuitry 122. In one embodiment, monitoring circuitry 122 includes decoupling switching or filtering (not shown) to protect the monitoring circuitry 122 from the therapeutic signaling applied to the electrodes 118. In one embodiment, patient interface 116 includes an MVT effectiveness sensor 124 coupled to monitoring circuitry 122. MVT effectiveness sensor 124 can measure observable patient characteristics that are related to the patient's condition. In one example embodiment, MVT effectiveness sensor 122 is a fingertip pulse oximeter. In another embodiment, MVT effectiveness sensor 122 is a sonic arterial pulse sensor. In another example embodiment, MVT effectiveness sensor 122 is a gas sensor, such as an end tidal $CO_2$ sensor. In another embodiment, MVT effectiveness sensor 122 is a non-invasive sensor adapted to measure blood pressure.

AED 100 also preferably includes a rescuer interface 126 operatively coupled with controller 106. In one embodiment, rescuer interface 126 includes at least one pushbutton, and a display device for indicating at least the operational status of AED 100. In a related embodiment, rescuer interface includes a system for providing visual or audible prompting or instructions to the rescuer. In another embodiment, rescuer interface 126 includes a plurality of human-operable controls for adjusting the various AED operational parameters, and a display device that indicates measurements made by monitoring circuitry 122.

Figure 1B:
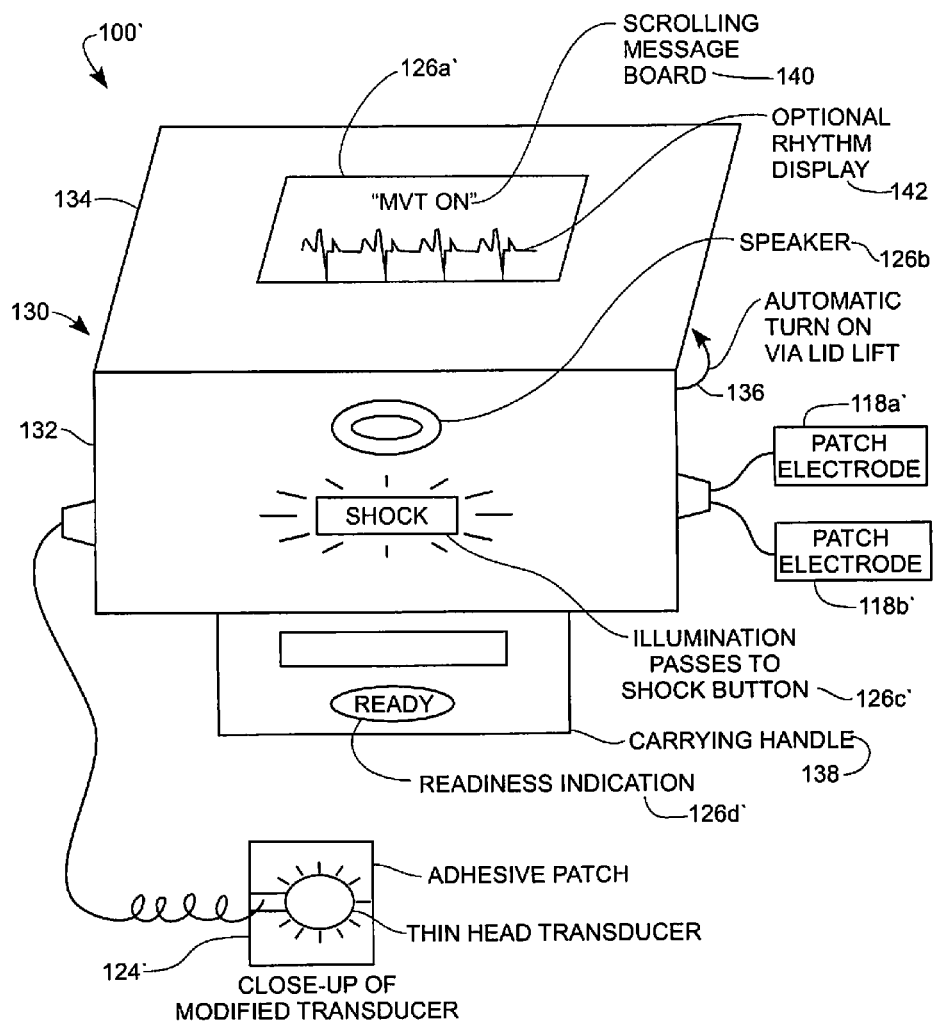
FIG. 1B is a diagram illustrating physical embodiment of the AED embodiment of FIG. 1A.
Figure 1C:
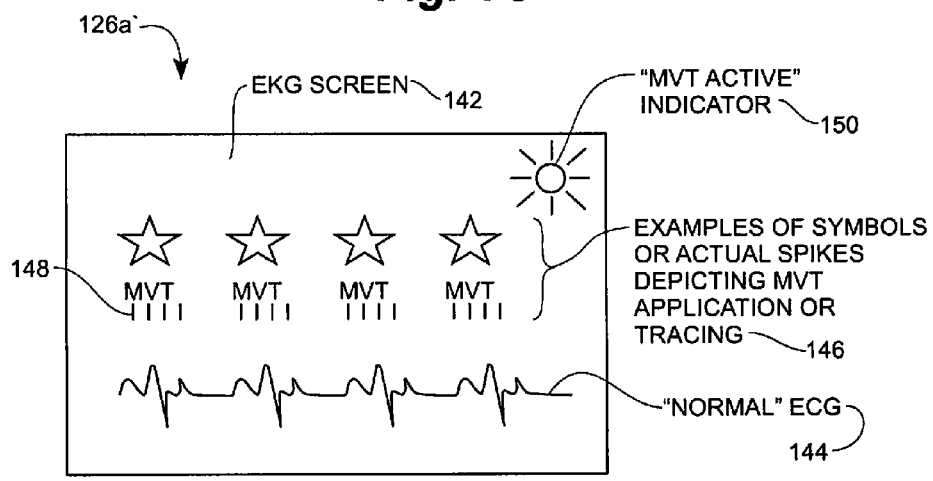
FIG. 1C illustrates an optional display that is part of the AED embodiments of FIGS. 1A and 1B, for use by a human rescuer.

FIG. 1B is a diagram illustrating human interface portions of example AED 100' according to one embodiment. AED 100' is a physical implementation of AED 100 (FIG. 1A). AED 100' is housed in a lightweight portable housing 130. Housing 130 includes a base portion 132 and a lid portion 134 that is attached to base portion 132 with a swiveling hinge. In one embodiment, AED 100' includes a lid state mechanism 136 that recognizes when the lid portion 134 is open and closed. For example, lid state mechanism 136 can include a Hall effect sensor in the base portion 132 that is placed near a permanent magnet that is situated in the lid portion 134 when the lid is closed, and is placed relatively far from the magnet when the lid is open. In another example embodiment, lid state mechanism is a mechanical switch that makes or breaks a contact depending on whether the lid is open or closed. Base portion 132 includes a carrying handle 138 to facilitate portability of AED 100'. Alternatively, buttons or switches could be used in place of the lid state mechanism 136. AED 100' includes four types of rescuer interfaces generally referred to herein as rescuer interface 126'. Optional display 126a' can include a scrollable textual display capability 140 that displays the operational status of AED 100', as well as written instructions to the rescuer. Also, optional display 126a', can include a graphical display functionality 142 that displays measured ECG waveforms, for example. In a related embodiment, the graphical display functionality 142 provides an indication that identifies points along the displayed ECG during which the MVT signals are administered. FIG. 1C illustrates an example of this embodiment. Graphical display portion 142 of display 126a' includes a measured ECG waveform trace 144. Additionally, graphical display portion 142 includes a set of visual indicators 146 that provide a time indication relative to the ECG waveform trace 144 of each MVT application. As described in greater detail below, an MVT signal can include packets of individual pulses. Visual indicators 146 can include packet indicators 148, each corresponding to the application of a MVT packet. Visual indicators 146 can also include a global MVT indicator 150 that is active during actual MVT application to indicate that MVT is generally being applied.

After each MVT packet is delivered the EKG sense amplifiers will be opened (their inputs must be shorted during the MVT to prevent overload). In one embodiment, the amplifier output is ignored for 50 ms following MVT, to allow the amplifier and filters to stabilize. During the 200-800 ms until the next MVT packet, the method analyzes the rhythm in case the heart has returned to normal rhythm. While MVT is not delivered for the purposes of converting a VF to a normal rhythm, in at least some cases MVT may be able to convert VF to a stable or normal rhythm.

Unfortunately, the conventional rate-counting techniques of present AEDs for determining normal cardiac rhythms cannot be used with short observation windows such as 200 ms. Hence, a preferred embodiment of the present invention stores the EKG sample and performs a correlation analysis. First, an autocorrelation is done to see if the sample is itself internally somewhat repetitive which is what should be expected for NSR (normal sinus rhythm) especially for a longer sample period. The sample is then correlated with the previous 3 samples. If there is a strong correlation then it can be assumed that the patient is now back into NSR or has had their rhythm converted to a monomorphic tachycardia. In either case, the system will then halt the MVT and perform a longer more conventional analysis of the rhythm to guide further therapy. If it is found that the rhythm is now NSR then the system will generally completely stop therapy delivery. However, this may be overridden by a cardiac output sensor or the operator as EMD may have a NSR appearing rhythm but not cardiac output. If it is found that the rhythm is actually a VT or VF, then the AED preferably will go back to MVT and will no longer bother "peeking" to see whether the rhythm is NSR in response to MVT. In an alternate embodiment, the AED can continue MVT therapy for a given period of time, for example 10 seconds, followed by a periodic break of a shorter period of time, for example 1.5 seconds, in which the AED would see whether the rhythm is in NSR in response to MVT using more conventional techniques that require a longer observation window during the periodic breaks than the correlation embodiment as previously described.

Referring again to FIG. 1B, AED 100' also includes a speaker 126b' that is driven by an amplifier circuit coupled with a digital to analog (D/A) circuit, which, in turn, is integrated, or interfaced with, the system microprocessor (not shown). Speaker 126b' provides audible voice prompts to the human rescuer. AED 100' also includes a pushbutton 126c' that the rescuer can activate. During a rescue, the rescuer generally needs to make physical contact with the patient at certain times, and stand clear of the patient at different times. Prompting the rescuer to press pushbutton 126c', in response to an instruction to stand clear and push the button, provides an indication to AED 100' that the rescuer is clear of the patient. In one embodiment, the pushbutton 126c can be selectively illuminated to provide an additional visual indication to the rescuer. Readiness indicator 126d' is a nonvolatile visual indicator that continuously displays the operability status of AED 100'.

AED 100' includes two types of patient interface. First, electrodes 118a' and 118b' are adapted to be adhesively coupled to the patient's skin. In one embodiment, the adhesive consists of an electrically conductive gel. Electrodes 118a' and 118b' can be used to measure the patient's cardiac rhythm, and to apply MVT and defibrillation therapy to the patient. Second, MVT effectiveness sensor 124' includes a transducer adapted for measuring one or more vital signs of the patient, such as arterial pulse activity measured by way of pressure sensing, or by way of Doppler ultrasound technology. In one embodiment, the MVT effectiveness sensor is the transthoracic impedance as the chest impedance changes with cardiac output. In one embodiment, MVT effectiveness sensor 124' is integrated with an adhesive patch adapted to be attached to the patient's skin. In a related embodiment, the transducer portion of MVT effectiveness sensor 124' is implemented in a thin-or-thick-film semiconductor technology. Examples of suitable sites for arterial pulse sensing include the patient's aorta, femoral arteries, carotid arteries, and brachial arteries. Other accessible arteries may also be suitable. In one example embodiment of AED 100', the measurement collected via MVT effectiveness sensor 124' is displayed, substantially in real-time, on display 126'. The displayed measurement can be numerical or graphical, such as a bar-type or chart recorder-type display.

Figure 1D:
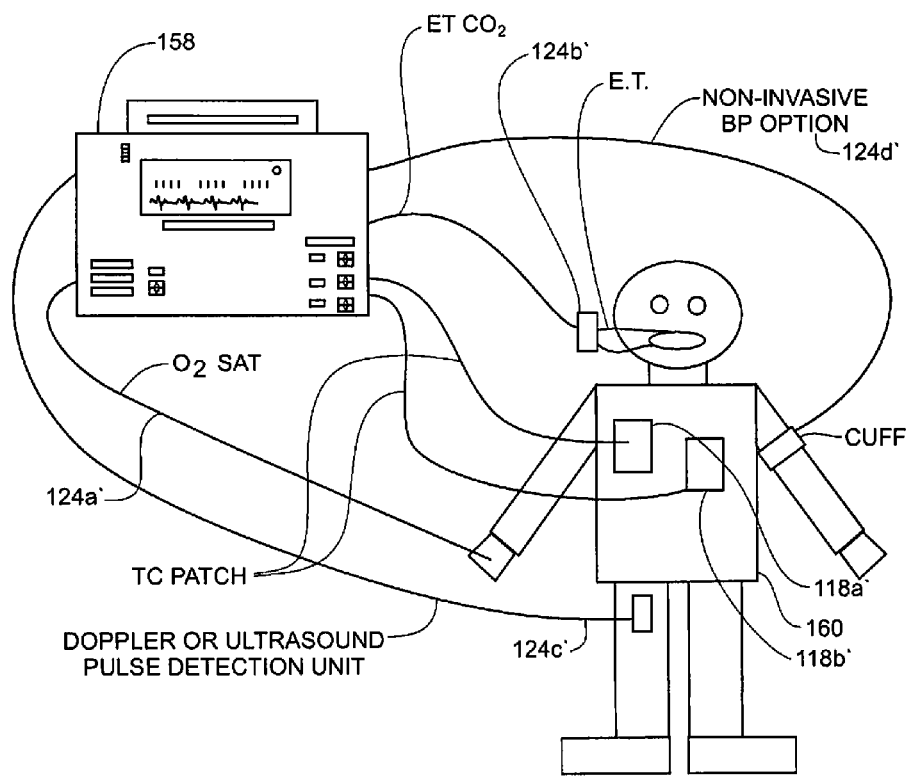
FIG. 1D illustrates various portions of a patient interface that is part of the AED embodiments of FIGS. 1A and 1B.

FIG. 1D illustrates examples of various types of patient interfaces between example AED 158 and patient 160. Note that these patient interfaces are not mutually exclusive, and could be used collectively in one embodiment. Electrodes 118a' and 118b' are shown attached to the chest of patient 160. An $O_2$ saturation sensor 124a' is attached to the fingertip, or elsewhere of patient 160. End tidal $CO_2$ sensor 124b' is attached to the endotracheal tube or mouth of patient 160 to monitor gasses exhaled by the patient 160. Pulse detection unit 124c' is shown attached to monitor the femoral artery of patient 160. Blood pressure sensor 124d' is shown attached to the arm of patient 160. In an alternative embodiment from the one illustrated in FIG. 1D, the $O_2$ saturation sensor 124a', end tidal sensor 124b', and pulse detection unit 124c', are battery-powered and are adapted to communicate measurement data via wireless radio frequency link. For example, Bluetooth technology could be utilized to accomplish close-range wireless data communications.

In operation, AED 100 is interfaced with the patient via leads 118a/118b, and MVT effectiveness sensor. In one embodiment, AED 100 provides guidance to a rescuer, via rescuer interface 126, for properly interfacing with the patient. AED 100 measures the patient's condition using monitoring circuitry 122 and at least a portion of the patient interface 116. Next, AED 100 analyzes the measured patient's condition to determine the existence of any indications for treating the patient. If the patient exhibits a condition treatable by AED 100, the device determines the type of therapeutic signal to apply to the patient, and proceeds to apply the treatment. The therapeutic signal can be an MVT signal, CPR prompt, or a defibrillation signal, either of which is delivered via discharge circuit 108 and leads 118a/118b.

During a rescue process, AED 100 provides prompting or instructions to a rescuer for facilitating the therapy and for protecting the rescuer's safety.

Pilot studies have indicated that MVT can provide coronary perfusion approaching levels that are associated with successful defibrillation and return of spontaneous circulation (ROSC). This coronary perfusion is believed to prepare the myocardium for defibrillation. In order to achieve this therapeutic effect, certain MVT signal attributes and ranges have been developed. FIG. 2 illustrates one example embodiment of a portion of an MVT signal waveform. The example signal waveform includes a train 200 of periodic packets of pulses. Three packets of pulses are illustrated: 202*a*, 202*b*, and 202*c* (generally referred to herein as pulse packets 202). Time duration 204 represents a duration of each pulse packet 202. Time duration 206 represents a period, or the inverse of the frequency, of the packets in pulse packet train 200. Equivalently, the characteristics of pulse train 200 can be defined by either time duration 204, 206 in conjunction with a duty cycle indication.

Each pulse packet 202 includes a periodic series of individual pulses 208*a*-208*d* (referred to generally herein as pulses 208). Each pulse 208 has a pulse duration 210, and the pulses in a pulse packet 202 have a period 212, which is the inverse of the repetition rate of pulses 208. Also, each pulse has an amplitude, as indicated at 214.

To produce the example signal waveform illustrated in FIG. 2, the example AED 100 of FIG. 1A can have the specifications presented below in Table 1:

TABLE 1

Example System specifications.

| Item | Specification |
| --- | --- |
| Pulsed Output Voltage | 20-1000 V |
| Output Load | 25-150 Ω |
| Pulsed Output Current | 100 mA-10 A |
| Pulsed Packet Rate | 20-180 packets/min |
| Pulsed Packet Duration | 10-200 ms |
| Intra-Packet Pulse Duration | 200 µs-10 ms |
| Intra-Packet Pulse Rate | 20-500 Hz |

Example AED 100 preferably can also administer biphasic defibrillation pulses of up to 200 J at a selected voltage in the range of 1000-2000 V.

In one example resuscitation utilizing AED 100, an MVT signal is administered to a patient experiencing ventricular fibrillation. The MVT signal has periodic packets of pulses 200, each pulse packet 202 having a 100 ms duration 204 and an amplitude 214 of approximately 250 volts. In response to the MVT signal, a large fraction of the patient's cardiac cells in ventricular fibrillation pass through a diastolic phase (phase 4) and are captured during any given 100 ms period. The phase 4 cells contract while those "captured" phase 3 cells prolong their contraction generating some cardiac output and thus producing coronary perfusion. Even though the phase 3 cells are already contracted at the time of the pulse, the pulse extends their contraction so that they do not relax and reduce the cardiac output being generated by the newly contracting cells. Because the voltage 214 is well above the transthoracic diastolic pacing threshold and is sufficient to facilitate the coronary perfusion described above, this example of MVT is different than pacing. The result of chopping each packet 202 into many shorter pulses 208 achieves sympathetic nerve stimulation that in turn increases cardiac myocyte contractility and excitability. This also increases skeletal muscle and phrenic nerve stimulation (which drive the left and right sides of the diaphragm).

Each of the parameters listed in Table 1 above has an effect on cardiac cell capture, and on sympathetic stimulation of the patient. The stimulation time constants for each of these objectives are quite different. Sympathetic, skeletal (in the chest and the abdomen), and phrenic nerve stimulation has a short time constant and is therefore associated with shorter pulse durations 210 and multiple pulses in a relatively long pulse packet 202. On the other hand, cardiac stimulation is characterized by longer time constants, suggesting increased pulse durations 210 and a packet 202 of a single pulse. Selecting MVT parameters for the desired type of electrical stimulation is preferred. For example, in the case of stimulating coronary perfusion, short packet duration will capture fewer cardiac cells going through phases 3 and 4. Conversely, longer packet durations will reduce the time allowed for the cardiac cells to relax. Finally, the repetition rate (packet period) may need to vary to achieve an optimal coronary perfusion effect.

One important aspect of the invention is to achieve a best possible therapeutic effect of the MVT on the patient. Accordingly, in one example embodiment, the MVT amplitude, pulse rate, pulse time, and pulse train parameters are each optimized to the extent possible based on their actual effect on the patient. In this embodiment, monitoring circuitry 122 monitors a physiological indicator in the patient via MVT effectiveness sensor 124 that corresponds to the therapeutic effect of administering the MVT. In one example embodiment, the physiological indicator is measured with a surrogate marker of coronary perfused pulse (CPP) such as fingertip pulse oximetry. In another example, a surrogate marker of CPP is end tidal $CO_2$. In an alternative embodiment, the physiological indicator is a direct indicator of CPP. For example, an ultrasonic Doppler-type sensor can be used as MVT effectiveness sensor 124 to measure characteristics of arterial pulses in the patient caused by the MVT.

In one embodiment, each of the MVT signal parameters is varied while observing the effect of the parameter variance on the monitored physiological indicator. For example, Table 2 below indicates variable MVT signal parameters and corresponding ranges of values where the optimal settings may be found to achieve coronary perfusion in a particular patient.

TABLE 2

Ranges of Optimal Parameter Values to Achieve CPP.

| Variable Parameter | Optimal Range |
| --- | --- |
| Pulsed Output Voltage | 75-300 V |
| Pulsed Output Current | 500 mA-6 A |
| Pulsed Packet Rate | 70-100 packets/min |
| Pulsed Packet Duration | 80-120 ms |
| Intra-Packet Pulse Duration | 2-6 ms |
| Intra-Packet Pulse Rate | 30-75 Hz |

Each of these parameters of Table 2 has an impact with regard to cardiac cell capture and nerve (sympathetic, nodes of Ranier driving skeletal muscles, and phrenic) stimulation. The stimulation time constants for each of these objectives are different. Sympathetic muscle stimulation is associated with shorter pulse durations and multiple pulses in a long pulse packet. Cardiac stimulation is associated with longer pulse durations and a single pulse. Optimization of the packet duration for the electrical stimulation is preferred. A short packet duration will capture fewer cardiac cells going through phases 3 and 4. Conversely, longer packet durations will reduce the time allowed for the cardiac cells to relax. Finally, the repetition rate (packet period) for optimal coronary perfusion needs may vary.

The following description provides an example of one method of operating an external defibrillator according to one embodiment of the present invention. First, a human rescuer places the electrodes on the victim's chest. The electrodes preferably will be adhesively bonded to the patient's skin by a conductive gel. The rescuer places a pulse oximeter on the victim's fingertip. The AED will evaluate the patient's condition to determine whether any MVT or defibrillation can benefit the patient. If the patient is experiencing a treatable condition, such as ventricular fibrillation, the AED will apply MVT that will initially be delivered at the predefined default settings presented in Table 3 below.

TABLE 3

Initial MVT Parameter Settings

| Variable Parameter | Optimal Range |
| --- | --- |
| Pulsed Output Voltage | 250 V |
| Pulsed Output Current (depends on the resistance) | 1-A-5 A |
| Pulsed Packet Rate | 90 packets/min |
| Pulsed Packet Duration | 100 ms |
| Intra-Packet Pulse Duration | 4 ms |
| Intra-Packet Pulse Rate | 100 Hz |

Next, the MVT parameters of Table 3 are varied over a first time duration of 0.25-1.5 minutes, and the effect of the various MVT settings on the pulse oximetry signal is recorded against the respective settings. The settings corresponding to the optimal therapeutic effect are then selected, and MVT is applied during a longer second period of up to 2 minutes or more. Next, the AED will evaluate a need for applying a defibrillation shock. For example, the MVT can be suspended in a third period of time during which the patient's cardiac rhythm is analyzed. If the analysis indicates the patient's rhythm is shockable, the defibrillation signal is administered. Following the defibrillation shock, the patient's cardiac rhythm is briefly analyzed, and the MVT can be applied again according to the previously-determined optimal settings, if needed. In a related embodiment, the AED can charge its defibrillation energy storage capacitors during the later stages of the MVT to avoid delays associated with energizing the charge circuit after the need for defibrillation has been established.

Due to the time criticality of the pre-defibrillation period, the parameter variation and selection must be done intelligently. Besides the default values, the exploratory parameters are as follows:

Pulsed Packet Durations of 10, 30, 55, 85, 115 and 150 ms;
Pulsed Packet Rates of 40, 75 and 150 pulses per minute;
Intra-Packet Pulse Durations of 2, 5 and 10 ms. (i.e., Pulse ON time); and
Intra-Packet Pulse OFF times of 0.5 and 2 ms.

The "OFF" times combined with Intra-Packet Pulse Durations, will provide Intra-Packet Pulse Rates of 83.3, 95.2, 142.9, 181.8, 250, 400 Hz with duty cycles of 83.3%, 95.2%, 71.4%, 90.9%, 50%, 80.0%, respectively.

In one example embodiment, a quadratic multi-regression model (with term interaction) is utilized to predict the CPP from the parameter settings. The AED will then set the parameters to the predicted peak output settings. Alternatively, in another example embodiment, the parameters are varied using a "simplex" method which will adjust the parameters in multidimensional space and converge on the optimum settings. With the simplex method, 3 points are chosen in multidimensional "parameter space" and tried for CPP. The point with the highest CPP is probably going to be the closest to the best point. The direction in which to select the next point to try is given by the 2 worst points. The simplex method calculates the midpoint of the two worst points. A line is then drawn from this midpoint to the "best" point and a little beyond to find the next point to try. The worst of the 4 points is discarded and the simplex method is repeated with the remaining 3 points.

In a related embodiment, the AED provides audible or visual instructions to the rescuer. If the patient has been down a very long time, it may be necessary to give a few manual chest compressions before the MVT can give effective electrical CPR. The effect of such manual chest compressions would "prime the pump." Accordingly, one instruction can include prompting the rescuer to administer manual chest compressions to the patient prior to automatically administering MVT. In another embodiment, the AED permits the operator to override the MVT in the case where it is known that the patient has been down only a minute or two. In this case, the resuscitation procedure would proceed immediately to waveform analysis, capacitor charging, and shock delivery.

In another example embodiment, a fractal calculation known as a "scaling exponent" is utilized to estimate the extent of deterioration of the patient's heart based on monitored patient characteristics. U.S. Pat. No. 6,438,419, entitled "Method and Apparatus Employing a Scaling Exponent for Selectively Defibrillating a Patient," describes the use of a scaling exponent, and is incorporated herein by reference. The scaling exponent would be calculated from the electrical signal from the chest electrodes. If the scaling exponent calculation produces a relatively high value, then the AED can instruct the human rescuer to, for example administer 15 manual chest compressions. Another variation of the device includes utilizing other waveform characteristics such as amplitude, frequency or coarseness. The following steps of Table 4 exemplify such a process.

TABLE 4

Example Process utilizing s Scaling Exponent Calculation

| Step | Decryption |
| --- | --- |
| 1 | Place the electrodes on the victim's chest. |
| 2 | Place the pulse oximeter on the victim's fingertip. |
| 3 | Calculate scaling exponent (SE). |
| 4 | If SE < 1 go to step 10 |
| 5 | If SE > 2 ask for 15 manual chest compressions and go to step 7 |
| 6 | If 1 < SE < 2 then go directly to step 7 |
| 7 | Apply medium voltage therapy which will be delivered at default settings. |
| 8 | Vary the following MVT parameters: packet duration, repetition rate of the packet, intra-packet pulse width and intra-packet stimulation frequency (i.e. intra-packet duty cycle). Record the effect of various MVT parameters on the pulse oximetery signal. |
| 9 | Select the optimal parameters and deliver the MVT for 2 minutes. |
| 10 | Apply defibrillation shock. If successful, stop. Otherwise return to step 3. |

In another embodiment, AED 100 is used to administer MVT for electrically forcing respiration in the patient. Table 5 below presents ranges of optimal MVT parameters for achieving respiration in the patient.

TABLE 5

Ranges of Optimal Parameter Values to Achieve Respiration.

| Variable Parameter | Optimal Range |
| --- | --- |
| Pulsed Output Voltage | 75-300 V |
| Pulsed Output Current | 50-500 mA |
| Pulsed Packet Rate | 10-30 packets/min |
| Pulsed Packet Duration | 0.5-3 seconds |
| Intra-Packet Pulse Duration | 50-200 us |
| Intra-Packet Pulse Rate | 25-150 Hz |

The effect of these MVT signals is to stimulate the patient's phrenic nerve and/or diaphragm, and to cause controlled muscle contraction in the patient's chest wall and abdomen, thereby eliciting a response that produces ventilation. Performance can be improved with separate sets of electrodes having an optimal placement on the patient's exterior. It will be understood that stimulation of the phrenic nerve preferably utilizes two sets of electrodes positioned across the top of the patient's chest. Alternatively, a second set of electrode can be placed, for example, across the patient's shoulder region. In order to draw air into the patient's lungs, the muscles, especially the abdominals, are minimally stimulated while the patient's diaphragm descends to create a negative pressure. An MVT effectiveness sensor for facilitating forced respiration utilizing MVT can include a $CO_2$ sensor for directly monitoring the patient's ventilation activity as well as an $O_2$ saturation detector.

Figure 3:
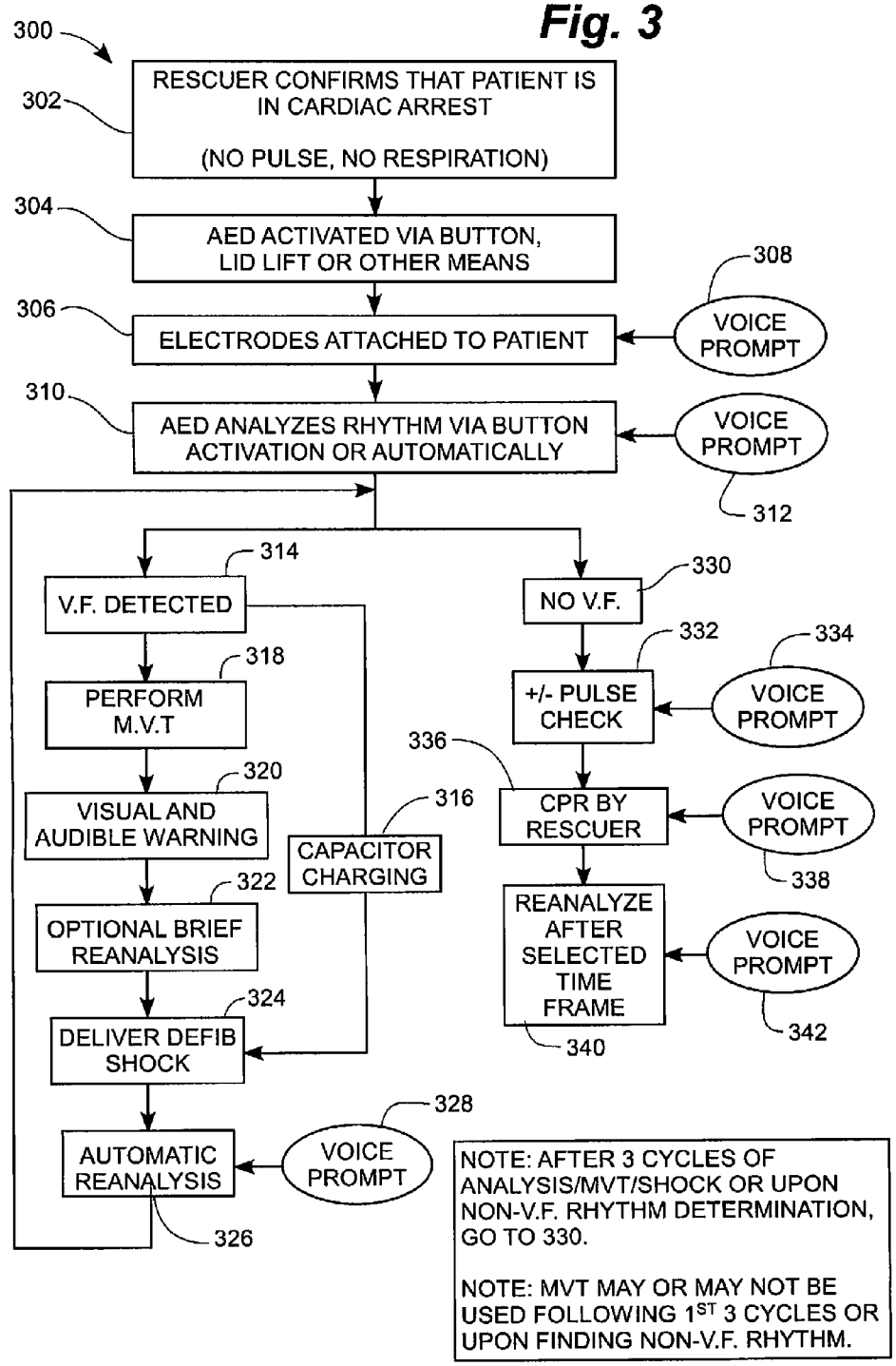
FIG. 3 is a flow diagram illustrating a rescue sequence according to one aspect of the invention that incorporates MVT and defibrillation therapy.
Figure 4:
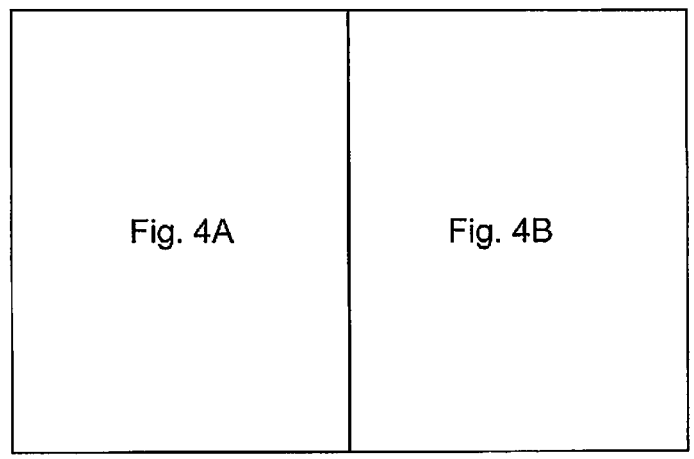
FIG. 4 is a flow diagram illustrating a rescue sequence according to one aspect of the invention that incorporates MVT and defibrillation therapy, as well as a predictive determination of the patient's responsiveness to defibrillation therapy.
Figure 4B:
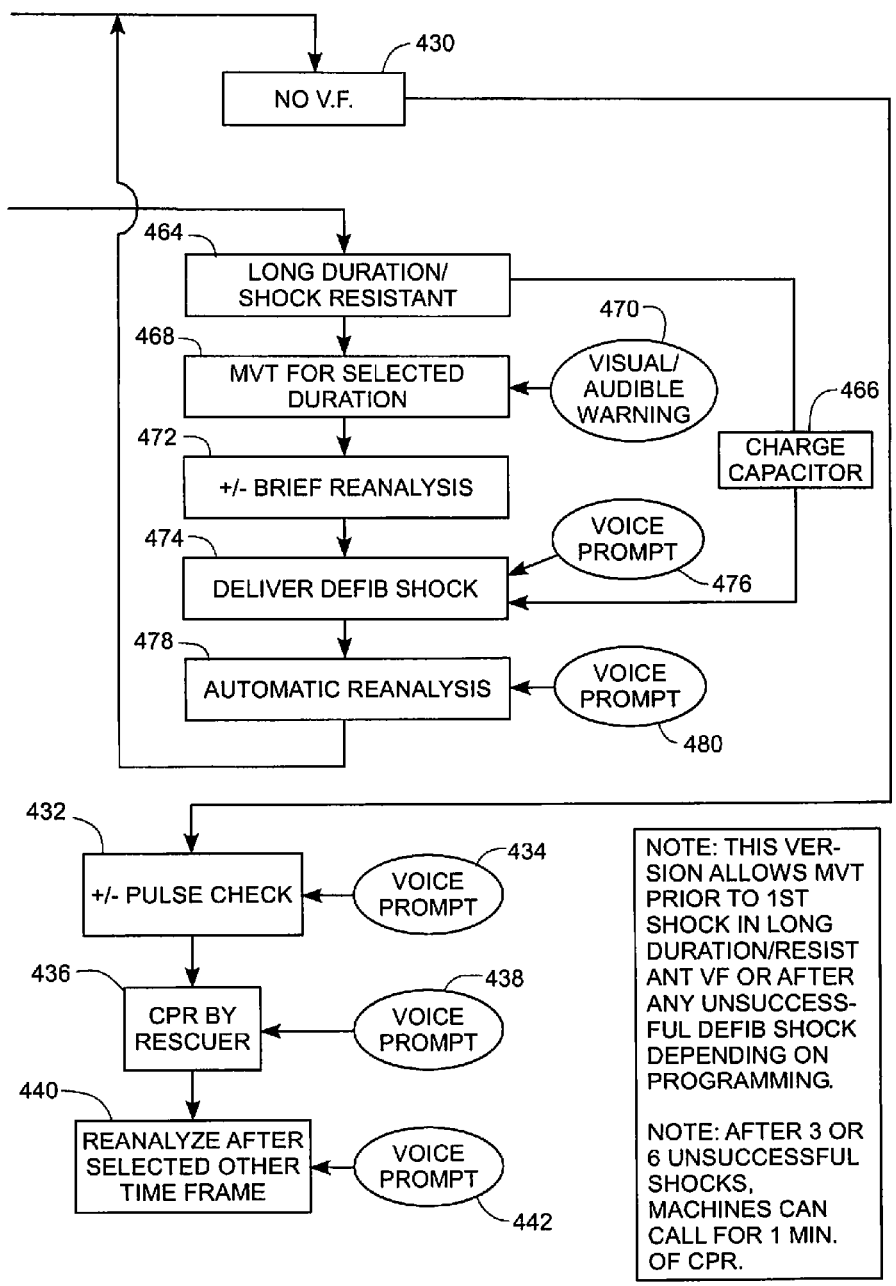

The therapeutic delivery by an AED of multiple pulses of energy below the defibrillation threshold and above the cardiac pacing upper limit to produce coronary perfusion and respiration during cardiac arrest, as a substitute for CPR, is the novel therapeutic effect that is the focus of the preferred embodiment of the present invention. The manufacture of an AED that can generate blood flow and oxygen distribution during cardiac arrest would provide a distinct clinical advantage over devices that provide only defibrillation therapy. FIGS. 3-5 illustrate various embodiments of operating an AED that includes MVT functionality.

FIG. 3 is a flow diagram illustrating an example operational sequence 300 in which MVT is integrated as part of an example AED therapy routine. At 302, a human rescuer confirms that the patient is in cardiac arrest. Symptoms would include no pulse and no respiration. At 304, the AED is activated. Activation can include opening the lid or actuating a switch or button by the rescuer. At 306, the rescuer attaches the AEDs electrodes and other patient interface devices to the patient based on voice prompt instructions provided by the AED at 308. At 310, the AED analyzes the patient's cardiac rhythm to assess whether the patient has a condition that is treatable by the AED. Voice prompts are provided to the rescuer at 312 to stand clear of the patient so as not to interfere with the analysis. Assuming a treatable condition, such as ventricular fibrillation, has been detected (314), the AED begins charging its high-voltage capacitors in preparation for administering the high-energy defibrillation signal. Meanwhile, at 318, the AED initiates MVT. A visual and audible warning is simultaneously given to the rescuer at 320 to stand clear while MVT and possibly, the defibrillation shock, are administered. Optionally, as indicated at 322, a quick re-analysis may be performed to check the patient's condition in case the MVT, alone, was successful in reviving the patient or in case the patient no longer exhibits a shockable condition. At 324, if appropriate, the defibrillation signal is applied. Following the defibrillation attempt, at 326, the patient's condition is analyzed again, and the rescuer is given an instruction via voice prompt at 328 to stand clear to avoid interfering with the analysis. The process is repeated beginning at 310 if the defibrillation attempt was unsuccessful at resuscitating the patient. The AED may be configured to omit the MVT during one or more subsequent repetitions of the automatic therapy (314-328). After three failed defibrillation attempts, or upon detection of a non-shockable cardiac rhythm, the AED will prompt the rescuer to manually intervene.

If no ventricular fibrillation was exhibited by the patient (330), the AED enunciates a voice prompt at 334 instructing the rescuer to stand clear while the AED verifies the patient's pulse, and to administer manual CPR (336, 338) if needed. After a certain time duration, the patient's condition is re-analyzed at 340. Simultaneously, at 342, the rescuer is instructed to stand clear.

An alternative AED rescue routine 400 is illustrated in FIG. 4. At 402, a human rescuer confirms that the patient is in cardiac arrest. Symptoms would include no pulse and no respiration. At 404, the AED is activated by the rescuer. Activation can include opening the lid or actuating a switch or button. At 406, the rescuer attaches the AEDs electrodes and other patient interface devices to the patient based on voice prompt instructions provided by the AED at 408. At 410, the AED analyzes the patient's cardiac rhythm to assess whether the patient has a condition that is treatable by the AED. Voice prompts are provided to the rescuer at 412 to stand clear of the patient so as not to interfere with the analysis.

Assuming a treatable condition, such as ventricular fibrillation, has been detected (414), the AED next automatically analyzes the characteristics of the patient's condition to determine whether the patient has a treatable condition at 450. Characteristics analyzed at 450 can include the frequency of the patient's ventricular fibrillation condition, its amplitude, the scaling exponent, and the like. Also, the AED can prompt the rescuer to input the approximate time, if known, during which the patient has been down before initiating treatment with the AED. In one embodiment, the AED uses a microphone coupled to an amplifier, and an A/D circuit interfaced with the microprocessor, all of which functions as a voice recognition system for inputting the rescuer's response. If the AED determines that the patient has been down only a short duration, or that the patient exhibits a condition that is sufficiently likely to respond to electrical defibrillation (452), the capacitor is charged, and the defibrillation energy is administered preceded by a voice prompt to the rescuer to stand clear (456-58). At 460-62, the AED automatically performs analysis to measure the effect of the defibrillation treatment.

If, on the other hand, the AED determines that the patient is not in a suitable condition to receive a defibrillation shock right away, the AED first administers MVT, as indicated at 468. The MVT is preceded by an audible warning to the rescuer to stand clear (470). At 466, the charging is initiated for the defibrillation capacitors to avoid charging delay if a defibrillation shock becomes advisable. Following the MVT, the patient's condition is re-assessed briefly at 472. The brief re-assessment can include only a determination of pulselessness, and not a full cardiac rhythm analysis, in order to save time during this critical period. If a defibrillation shock is indicated, the shock is applied at 474, preceded by an audible warning to the rescuer (476). At 478, the patient's condition is re-analyzed to assess the effect of the defibrillation (478, 480). If the defibrillation is unsuccessful at resuscitating the patient, the process, optionally including MVT, is repeated, beginning at 414/430. After a specified number of failed defibrillation shocks, the AED can instruct the rescuer to perform manual CPR.

If no ventricular fibrillation was exhibited by the patient (430), the AED enunciates a voice prompt at 434 instructing the rescuer to stand clear while the AED verifies the patient's pulse, and to administer manual CPR (436, 438) if needed. After a certain time duration, the patient's condition is re-analyzed at 440. Simultaneously, at 442, the rescuer is instructed to stand clear.

FIG. 5 illustrates another example embodiment of an AED rescue sequence 500. This embodiment incorporates MVT for all patients in cardiac arrest, regardless of underlying rhythm. Example rescue sequence 500 features MVT performed prior to cardiac rhythm analysis. At 502, a human rescuer confirms that the patient is in cardiac arrest. Symptoms would include no pulse and no respiration. At 404, the AED is activated by the rescuer. Activation can include opening the lid or actuating a switch or button. At 506, the rescuer attaches the AED electrodes and other patient interface devices to the patient based on voice prompt instructions provided by the AED at 508.

At 510, the AED initiates MVT, accompanied by a visual or audible warning (512) to the rescuer to stand clear of the patient. MVT is performed for a preconfigured time, after which the AED performs cardiac rhythm analysis at 514 accompanied by a voice prompt 516 instructing the rescuer to stand clear. Performing MVT before rhythm analysis is believed to increase the patient's probability of survival because MVT, administered without delay, can improve the patient's vital condition as quickly as possible after the onset of cardiac arrest.

If rhythm analysis detects the presence of ventricular fibrillation at 518, the AED proceeds to administer a defibrillation shock, and re-analyze the patient's condition (520-28). If the AED fails to resuscitate the patient, the process can be repeated either with, or without, the MVT, as indicated at 530. If a rhythm analysis indicates that the patient is not experiencing ventricular fibrillation (532), the appropriate treatment would be to perform manual or automatic CPR on the patient. Accordingly, at 534, the AED can either administer electrical CPR using MVT signals, or prompt the rescuer to perform manual CPR. In one embodiment, the AED is capable of performing a more advanced assessment of the patient's condition, as described above with reference to FIG. 4. In this embodiment, the AED can be programmed to determine whether electrically-induced CPR, or manual CPT would be more beneficial. In a related embodiment, based on the assessed condition of the patient, the AED can automatically devise and implement a combined treatment plan utilizing electrical MVT stimulation alternated with manual CPR administered by the rescuer. At 536, following the selected CPR resuscitation attempt, the patient's cardiac rhythm is re-assessed.

Figure 6:
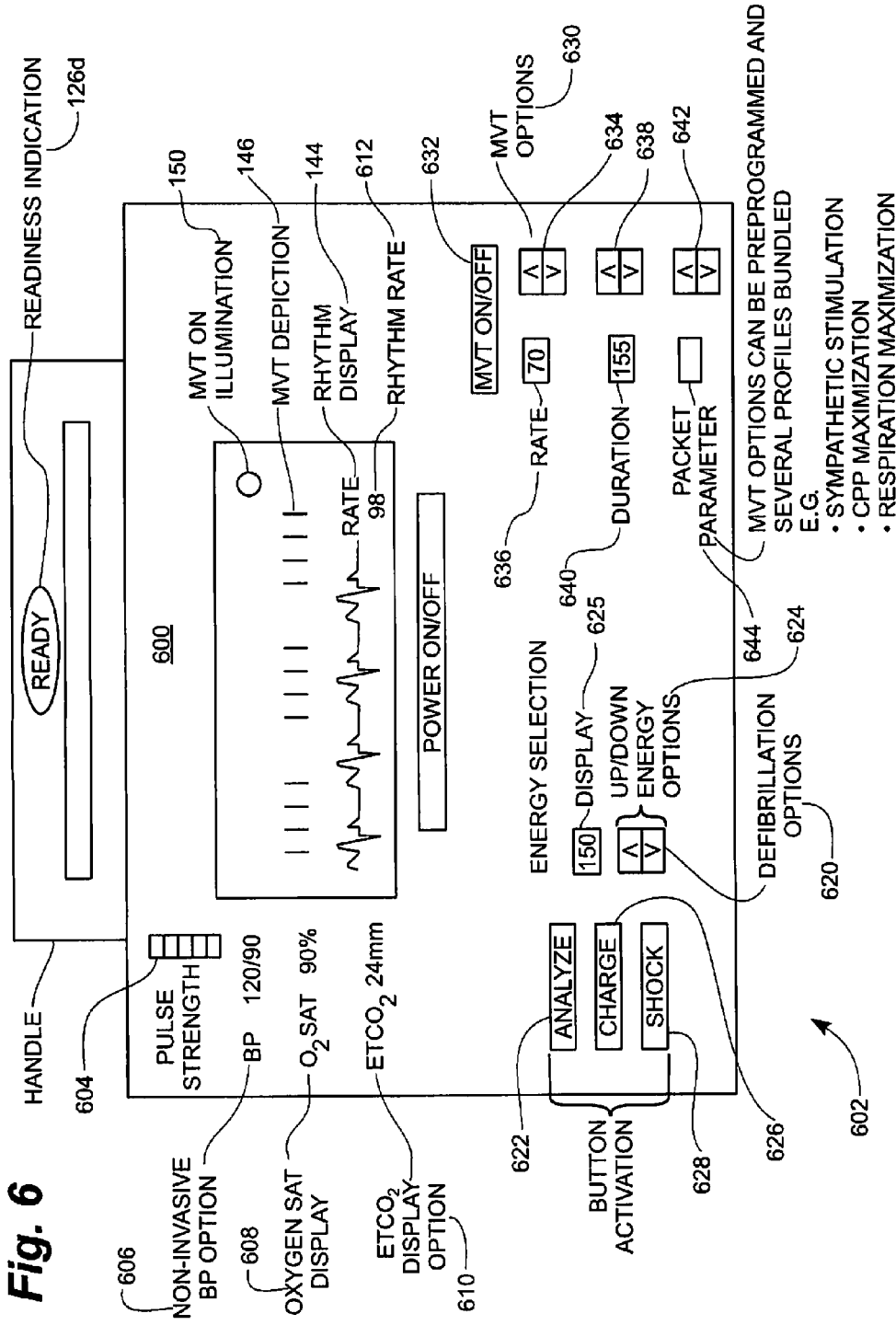
FIG. 6 is a diagram illustrating a rescuer interface of an advanced electrotherapy apparatus according to one aspect of the invention.

The embodiments described above exemplify aspects of the invention in the context of AEDs. AEDs are well suited for untrained or minimally-trained rescuers because of their high degree of automation. However, aspects of the invention can be advantageously applied in rescue equipment designed for advanced rescuers. FIG. 6 illustrates an example rescuer interface 600 of an advanced electrotherapy apparatus 602. Electrotherapy apparatus 602 is adapted to administer MVT, as well as defibrillation therapy to a patient experiencing cardiac arrest. In one embodiment, electrotherapy apparatus 602 is a hand-portable, battery-powered device. In another embodiment, electrotherapy apparatus 602 is a wheeled-portable, battery backup crash cart style device suitable for use in a medical facility. Still another embodiment of electrotherapy apparatus 602 is a bedside, battery backup device suitable for use in an intensive care unit, for example. Rescuer interface 600 provides indicators and rescuer-operable controls that permit the rescuer or medical personnel or staff to measure indicators of the patient's condition, and select the sequence and type of the electrotherapy. Also, rescuer interface 600 permits the rescuer to observe effectiveness of the electrotherapy and make adjustments to various parameters of the therapy.

Rescuer interface 600 includes pulse strength indicator 604. In one example embodiment of electrotherapy apparatus 602, pulse strength indicator 604 is operatively coupled with a pulse sensor that is capable of making a quantitative measurement of the patient's pulse. In one embodiment, as illustrated in FIG. 6, pulse strength indicator 604 is a graphical display that shows the intensity of each measured pulse on a linear scale. In another embodiment (not shown), pulse strength indicator 604 graphically displays the strength of each pulse on a two-dimensional coordinate system where one of the dimensions represents time, while the other dimension represents the measured pulse intensity.

Rescuer interface 600 also includes an indicator 606 that displays the measured blood pressure of the patient. Blood pressure indicator 606 is operatively coupled to a blood pressure measuring system that includes an inflatable cuff, such as sensor 124d' (FIG. 1D). In one embodiment, the blood pressure measuring system in integrated into electrotherapy apparatus 602. Oxygen saturation display 608 indicates a measurement made by an $O_2$ saturation sensor, such as fingertip pulse oximeter 124a' (FIG. 1D) interfaced with electrotherapy apparatus 602. End tidal $CO_2$ display 610 indicates a concentration of carbon dioxide in the patient's exhaled air. A $CO_2$ sensor, such as sensor 124b' (FIG. 1D) is interfaced with electrotherapy apparatus 602 to provide the measurement for display.

Rescuer interface 600 also includes a display of the patient's cardiac rhythm rate 612, and a graphical ECG display 144 (see also FIG. 1C). In one embodiment, both of these measurements are made using the electrotherapy application electrodes, such as electrodes 118a' and 118b' (FIG. 1D). The display portion of rescuer interface 600 also includes MVT depiction 146 and MVT active indicator 150, as described above with reference to FIG. 1C; as well as a nonvolatile rescuer indicator 126d' as described above with reference to FIG. 1B.

Rescuer-operable controls of rescuer interface 600 include controls 620 for defibrillation, and controls 630 for MVT. Defibrillation controls 620 include analyze initiation pushbutton 622, which instructs the electrotherapy apparatus 602 to initiate ECG analysis, which will be displayed on graphical ECG display 144. The rescuer can select the defibrillation signal energy using controls 624 and energy settings display 625. The rescuer can selectively charge the defibrillation energy storage circuit by actuating a charge pushbutton 626. Rescuer activation of shock button 628 will instruct the electrotherapy apparatus 602 to apply the defibrillation signal to the patient via the electrodes.

MVT controls 630 include MVT on/off pushbutton 632 for initiating and stopping the MVT. Pulse packet rate controls 634 allow the rescuer to configure the rate at which packets of MVT pulses will be administered. Rate setting display 636 indicates the present rate setting. Duration controls 638 allow the rescuer to select the duration of each MVT pulse packet applied to the patient. Duration setting display 640 indicates the present duration setting. The pulse packet rate controls 630 and duration controls 638 enable the rescuer to manually optimize the MVT to achieve the desired therapeutic effect in the patient. For example, if the rescuer wishes to perform CPR using MVT, the rescuer can use a first set of MVT parameters optimized for stimulating cardiac output, alternated in time with a second set of parameters optimized for stimulating respiration in the patient. Alternatively, the rescuer can select from among a pre-programmed set of MVT profiles corresponding to different types of therapeutic effects using semi-automatic MVT controls 642. In one embodiment, semi-automatic MVT controls 642 permit the rescuer to select among MVT profiles adapted for sympathetic stimulation, coronary pulse perfusion (CPP), or respiration. Each profile, when selected, will automatically control the MVT parameters to optimize, to the extent possible, the selected therapeutic effect. The set of selectable profiles can also include various combinations of the profiles mentioned above. For example, a CPR profile can alternate between forcing CPP and respiration using the MVT. Packet parameter display 644 indicates to the rescuer which MVT profile is selected.

The invention may be embodied in other specific forms without departing from the essential attributes thereof; therefore, the illustrated embodiments should be considered in all respects as illustrative and not restrictive.

What is claimed is:

1. An improved automated external defibrillator (AED), the AED including a set of electrodes that are adapted to interface with an exterior surface of a patient, defibrillation circuitry that is adapted to generate and deliver a defibrillation shock to the patient via the set of electrodes, patient monitoring circuitry that is adapted to sense a patient condition based on cardiac activity of the patient, and at least one controller interfaced with the patient monitoring circuitry and the defibrillation circuitry, the at least one controller including logic configured to determine if the patient condition is treatable by administration of the defibrillation shock and, if so, to control generation and delivery of the defibrillation shock, the improvement comprising:
additional logic in the at least one controller configured to recognize whether the patient condition is treatable by cardio-pulmonary resuscitation (CPR); and
electrical CPR circuitry interfaced with the at least one controller, and adapted to generate and deliver medium voltage therapy (MVT) via the set of electrodes in response to a recognition, by the at least one controller, that the patient condition t-hat-is treatable by CPR, the MVT being continuous for a duration on the order of minutes, and having amplitude and waveform characteristics to (a) electrically force mechanical pumping action of the patient's heart via electrical stimulation of cardiac muscle cells, and (b) mechanically force pumping action of the patient's heart via electrical stimulation of non-cardiac muscle cells resulting in compression of the heart, during that duration;
wherein the electrical CPR circuitry is adapted to produce the MVT having amplitude and waveform characteristics such that, in the electrically forced mechanical pumping action in (a), diastolic cardiac muscle cells are forced to contract during each of a plurality of intervals and systolic cardiac muscle cells are prevented from relaxing during those intervals, and between successive ones of the plurality of intervals the cardiac muscle cells are not forced.

2. The improved AED of claim 1, wherein the electrical CPR circuitry generates MVT having a waveform for electrically forcing mechanical pumping action in (a) that includes a plurality of packets of pulses, wherein each packet causes the diastolic cardiac muscle cells to contract and causes the systolic cardiac muscle cells to remain contracted for a duration longer than they would otherwise remain contracted in an absence of the MVT.

3. The improved AED of claim 1, wherein the MVT includes a waveform that is adapted to cause sympathetic nerve stimulation facilitating cardiac myocyte contractility and excitability in the patient.

4. The improved AED of claim 1, wherein the additional logic in the at least one controller is configured to selectively adjust at least one MVT control parameter controlling the generating and delivery of the MVT that affects at least one characteristic of the MVT selected from the group consisting of: a time duration between successive pulses, a pulse duration, a time duration between the first packet and the second packet, or any combination thereof.

5. The improved AED of claim 1, wherein the MVT includes at least one pulse having a time constant that is short enough to stimulate skeletal muscle tissue in the patient.

6. The improved AED of claim 1, wherein the improvement further comprises:
monitoring equipment operably interfaced with the at least one controller to automatically monitor an additional physiologic condition of the patient.

7. The improved AED of claim 6, wherein the monitoring equipment is configured to facilitate at least one type of automatic monitoring selected from the group consisting of: monitoring of a patient's fingertip pulse oximetry, monitoring of a patient's respiration, and monitoring of an arterial pulse of the patient.

8. The improved AED of claim 1, wherein the electrical CPR circuitry is adapted to produce the MVT having amplitude and waveform characteristics such that, in the mechanically forced pumping action in (b), a combination of physiologic effects is produced in the patient by the MVT to cause the mechanically forced pumping action of the patient's heart, the combination including a plurality of muscular contraction events in the patient's chest region, a plurality of muscular contraction events in the patient's abdominal region, and stimulation of the patient's phrenic nerve.

9. The improved AED of claim 1, wherein the AED further includes an operator interface that includes a graphical display interfaced with the at least one controller and wherein the improvement further comprises:
a display on the graphical display that includes a plot of an electrocardiogram (ECG) curve obtained from the patient, and an MVT application indicator plotted together with the ECG curve, the MVT indicator indicating at least one instance of MVT application relative in time to events represented by the ECG curve.

10. The improved AED of claim 1, wherein the same electrodes of the set of electrodes through which the defibrillation shock is delivered are used to deliver the MVT.

11. The improved AED of claim 1, wherein the at least one controller is configured to deliver the MVT while the defibrillation circuitry is charging up to deliver the defibrillation shock.

12. The improved AED of claim 1, wherein the MVT includes at least one waveform portion that has an amplitude of greater than 100 volts.

13. The improved AED of claim 1, wherein the MVT has amplitude and waveform characteristics to electrically force ventilation in the patient via the electrical stimulation of the non-cardiac muscle cells.

14. The improved AED of claim 1, wherein the duration during which the electrical CPR circuitry is configured to produce the MVT is at least two seconds.

15. The improved AED of claim 2, wherein within each packet of pulses, the intra-packet pulse duration is at most 10 milliseconds.

16. A hand-portable automated external defibrillator (AED) system comprising:
a set of electrodes that are adapted to interface with an exterior surface of a patient;
a patient monitoring sub-system that is operatively coupled to the set of electrodes and adapted to sense a patient condition based at least partly on cardiac activity of the patient;
defibrillation circuitry that is operatively coupled to the set of electrodes and adapted to generate and deliver a defibrillation shock to the patient via the set of electrodes in response to the patient condition sensed by the patient monitoring sub-system that is determined to be treatable by defibrillation;
electrical CPR circuitry that is operatively coupled to the set of electrodes and adapted to generate and deliver medium voltage therapy (MVT), via the same set of electrodes as those used for delivery of the defibrillation shock, in response to a patient condition sensed by the patient monitoring sub-system that is determined to be treatable by CPR;
at least one controller interfaced with the patient monitoring sub-system, the defibrillation circuitry and the electrical CPR circuitry, the at least one controller being configured to:
determine whether the patient condition sensed by the patient monitoring sub-system is treatable by either or both of the defibrillation or the CPR:
control generation and delivery of the defibrillation shock in response to a determination of the patient condition being treatable by defibrillation, and control generation and delivery of the MVT in response to a determination of the patient condition being treatable by CPR;
wherein the electrical CPR circuitry is configured to produce the MVT that is continuous for a duration on the order of minutes, and sufficient to cause both a hemodynamic effect and a respiratory effect in the patient during that duration, wherein the hemodynamic effect is achieved via:
targeted stimulation of cardiac muscle cells to electrically stimulate relaxed cells to contract and to electrically stimulate contracted cells to extend their contraction duration, and
targeted stimulation of non-cardiac chest muscle cells to electrically force chest compressions causing a mechanical pumping effect of the heart; and
wherein the respiratory effect is achieved via the targeted stimulation of the non-cardiac muscle cells to force some amount of ventilation;
wherein the electrical CPR circuitry is adapted to produce an MVT waveform targeting stimulation of the cardiac muscle cells having a pulsed packet output with intra-packet pulse widths of between 2 ms and 10 ms; and
wherein the electrical CPR circuitry is adapted to produce an MVT waveform targeting stimulation of the non-cardiac muscle cells having a pulsed packet output with intra-packet pulse widths of between 0.05 ms and 0.2 ms; and
wherein the electrical CPR circuitry is adapted to deliver the MVT having a pulsed output voltage of 75-1000 V, a pulsed output current of between 0.05-10.00 A, a pulsed packet rate of between 20-180 packets/minute, a pulsed packet duration of between 10-3000 ms, and an intra-packet pulse rate of between 20-500 Hz.

17. The AED system of claim 16 wherein the MVT waveform is targeted for generating a coronary perfused pulse and has a pulsed output with a voltage of between 75-300 V, a pulsed output current of between 0.5-6.0 A, a pulsed packet rate of between 70-100 packets/minute, a pulsed packet duration of between 80-120 ms, an intra-packet pulse duration of between 2.0-6.0 ms, and an intra-packet pulse rate of between 30-75 Hz.

18. The AED system of claim 16 wherein the pulsed output of the MVT is delivered multiple times by the at least one controller with varied parameter values and an initial parameter value of the pulsed output has a pulsed output voltage of about 250 V, a pulsed output current of between 1.0-5.0 A, a pulsed packet rate of about 90 packets/minute, a pulsed packet duration of about 100 ms, an intra-packet pulse duration of about 4.0 ms, and an intra-packet pulse rate of about 100 Hz.

19. The AED system of claim 16 wherein the MVT waveform that is targeted for generating a respiration effect and has a pulsed output voltage of between 75-300 V, a pulsed output current of between 50-500 mA, a pulsed packet rate of between 20-30 packets/minute, a pulsed packet duration of between 0.5-3.0 second, an intra-packet pulse duration of between 0.05 and 0.2 ms, and an intra-packet pulse rate of between 25-150 Hz.

20. The AED system of claim 16 wherein the patient monitoring sub-system further includes at least one component to monitor a measured effectiveness of the MVT and wherein the controller selectively adjusts at least one variable parameter of the pulsed output in response to the measured effectiveness.

21. The AED system of claim 20, wherein the at least one variable parameter of the pulsed output is selected from the group consisting of: the pulsed output voltage, the pulsed packet rate, the pulsed packet duration, the intra-packet pulse duration, and the intra-packet pulse rate.

22. The improved AED of claim 16, wherein the duration during which the electrical CPR circuitry is configured to produce the MVT is at least two seconds.

23. The AED system of claim 16 wherein the electrical CPR circuitry is configured to produce an MVT that is sufficient to stimulate the patient's phrenic nerve to cause a contraction in the diaphragm of the patient and thereby expand the chest, wherein the stimulation to contract the diaphragm is timed to alternate with MVT that stimulates the cardiac and non-cardiac muscles to thereby alternately draw blood into the heart while the heart is un-compressed, and pump blood out of the heart while the diaphragm is un-contracted.

* * * * *